United States Patent [19]

Bilstad et al.

[11] Patent Number: 4,582,598
[45] Date of Patent: Apr. 15, 1986

[54] REPLACEMENT FLUID CONTROL SYSTEM FOR A BLOOD FRACTIONATION APPARATUS AND THE LIKE

[75] Inventors: Arnold C. Bilstad, Deerfield; John T. Foley, Wheeling, both of Ill.

[73] Assignee: Baxter Travenol Laboratories, Inc., Deerfield, Ill.

[21] Appl. No.: 330,900

[22] Filed: Dec. 15, 1981

[51] Int. Cl.$^4$ .............................................. B01D 13/00
[52] U.S. Cl. ................... 210/101; 210/433.2; 210/927
[58] Field of Search ................. 422/48; 210/434, 929, 210/321.2, 927, 433.2, 101; 604/6; 73/223; 177/50

[56] References Cited

U.S. PATENT DOCUMENTS

| | | | |
|---|---|---|---|
| 3,375,357 | 3/1968 | Dekker et al. | 235/174 |
| 3,439,524 | 4/1969 | Rogers | 73/1 |
| 3,459,182 | 8/1969 | Naftulin | 128/214 |
| 3,557,789 | 1/1971 | Poitras | 128/275 |
| 3,579,441 | 5/1971 | Brown | 210/434 X |
| 3,655,123 | 4/1972 | Judson et al. | 233/21 |
| 3,665,169 | 5/1972 | Henderson et al. | 235/151.3 |
| 3,674,097 | 7/1972 | Gile | 177/3 |
| 3,684,875 | 8/1972 | Smith et al. | 235/151.33 |
| 3,701,106 | 10/1972 | Loshbough | 340/72.5 |
| 3,789,937 | 2/1974 | Strobel et al. | 177/210 |
| 3,802,432 | 4/1974 | Djerassi | 604/6 |
| 3,812,923 | 5/1974 | Rock | 171/1 |
| 3,853,267 | 12/1974 | Cadwell | 235/151.33 |
| 3,855,458 | 12/1974 | Motter et al. | 235/151.34 |
| 3,860,802 | 1/1975 | Knothe et al. | 235/151.33 |
| 3,890,969 | 6/1975 | Fischel | 422/48 X |
| 3,916,173 | 10/1975 | Williams, Jr. et al. | 235/151.33 |
| 3,960,224 | 1/1976 | Silvers | 177/47 |
| 4,008,405 | 1/1977 | Neumann et al. | 307/231 |
| 4,013,194 | 3/1977 | Moscarini | 73/223 X |
| 4,041,289 | 8/1977 | Brosh et al. | 235/151.33 |
| 4,044,846 | 8/1977 | Matilainen | 177/165 |
| 4,086,924 | 5/1978 | Latham, Jr. | 604/6 |
| 4,117,898 | 10/1978 | Moriyama | 177/165 |
| 4,139,069 | 2/1979 | Domis et al. | 177/1 |
| 4,144,943 | 3/1979 | Gallo | 177/50 X |
| 4,151,844 | 5/1979 | Cullis et al. | 128/214 R |
| 4,204,957 | 5/1980 | Weickhardt | 210/929 X |
| 4,243,532 | 1/1981 | Tsuda et al. | 210/434 X |
| 4,267,837 | 5/1981 | Purdy et al. | 128/275 |
| 4,294,320 | 10/1981 | Bilstad et al. | 177/1 |
| 4,320,855 | 3/1982 | Ricciardi et al. | 177/50 X |
| 4,330,837 | 5/1982 | Itani | 364/567 |
| 4,350,156 | 9/1982 | Malchesky et al. | 210/434 X |
| 4,370,983 | 2/1983 | Lichtenstein | 210/321.2 X |
| 4,372,846 | 2/1983 | Yamagami | 210/433.2 X |
| 4,397,747 | 8/1983 | Ikeda | 210/257.2 X |

OTHER PUBLICATIONS

Randall, "A New Uroflowmeter for Routine Clinical Use", from Bio. Med. Eng. (GB), vol. 1, No. 1, 1-1975, pp. 21-24.

Primary Examiner—Frank Spear
Attorney, Agent, or Firm—Eugene M. Cummings; Daniel D. Ryan; Bradford R. L. Price

[57] ABSTRACT

An apparatus for separating and collecting plasma from whole blood includes a ratio control system which enables replacement fluid to be added by a replacement fluid pump within the apparatus to processed plasma-deficient blood at a predetermined ratio to the volume of plasma collected in a collection container. A transducer within the system develops an electrical signal frequency-dependent on the weight of the collected plasma. This signal is applied through a first rate multiplier circuit to the up-count input of a bidirectional counter. A second signal derived from a tachometer on the replacement fluid pump is supplied through a second rate multiplier circuit to the down-count input of the counter. A digital-to-analog converter converts the count in the counter to an analog control signal which controls the operation of the replacement pump motor. The multiplication factors of the rate multipliers are set by a user-operated switch to obtain a desired replacement ratio. In an alternative autologous mode the replacement pump is connected to withdraw plasma from the collection container and the system varies the pump speed to maintain a constant collected volume in the container as plasma is withdrawn for processing and return to the donor.

7 Claims, 19 Drawing Figures

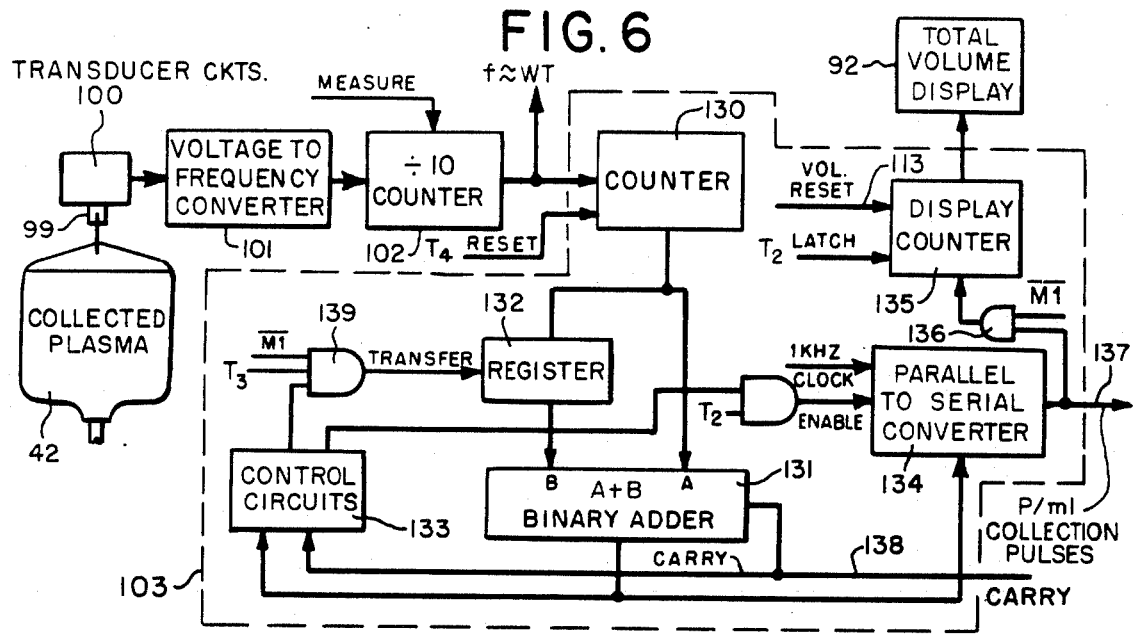
FIG. 6
FIG. 7
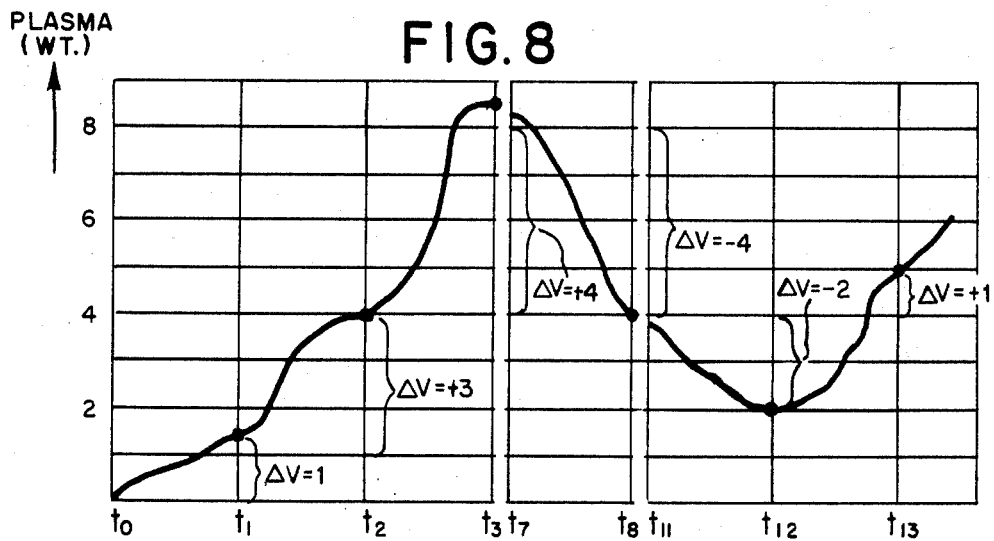
FIG. 8

(AUTOLOGOUS MODE)

REPLACEMENT FLUID CONTROL SYSTEM FOR A BLOOD FRACTIONATION APPARATUS AND THE LIKE

BACKGROUND OF THE INVENTION

The present invention relates generally to apparatus for processing whole blood, and more specifically to blood fractionation apparatus for separating and collecting a desired blood component, such as plasma.

Various methods and apparatus have been developed for the continuous flow processing of whole blood, wherein whole blood is taken from a live donor, a desired blood component is separated and collected, a replacement fluid is added to the processed blood, and the processed blood is returned to the donor. Blood components typically collected using such processing include plasma (plasmapheresis), white blood cells (leukopheresis) and platelets (plateletpheresis).

Continuous flow blood processing apparatus may be of the centrifugal type, wherein the differing density of the collected blood component causes the component to congregate for collection at a particular radial distance in a centrifuge, or may be of the filter type, wherein the particle size of the collected component allows only that component to pass through a filter membrane into a collection chamber. Filter type apparatus is generally preferable for continuous flow plasmapheresis applications, since such apparatus does not require complex rotating machinery and is more compact and less costly to manufacture.

One form of filter which is particularly attractive for use in plasmapheresis apparatus utilizes a plurality of parallel microporous hollow fibers arranged side-by-side in the form of a bundle within a hollow cylinder. As whole blood is caused to flow through the fibers the plasma component passes through the walls of the fibers to the surrounding container, which forms a collection chamber from which the component is transported to a collection bag. A preferred construction and method of manufacture of such a hollow fiber filter is shown in the copending application of Robert Lee and William J. Schnell, entitled, "Microporous Hollow Fiber Membrane Assembly and its Method of Manufacture", Ser. No. 278,913, filed June 29, 1981. A preferred form of apparatus for use in conjunction with such a hollow fiber filter is shown in the application of Arnold C. Bilstad and John T. Foley, "Blood Fractionation Apparatus", Ser. No. 330,898, now U.S. Pat. No. 4,447,191, filed concurrently herewith and incorporated herein by reference.

To preclude the collection of an excess of one blood component, such as plasma, from a donor, and consequent danger to the donor's health, it is highly desirable that the volume and collection rate of the blood component collected be monitored and maintained within prescribed limits. Preferably, the volume of the component actually collected and the rate of plasma collection should at all times be displayed in a digital form clearly readable by the operator. Prior art plasmapheresis apparatus relied on the weight of the plasma collection container to provide indications of collected plasma volume and plasma collection rate. One such apparatus is shown and described in the copending application of Arnold C. Bilstad and John T. Foley, entitled, "Apparatus and Method for Weighing Material Being Collected", Ser. No. 140,111, filed April 14, 1980, now abandoned.

One drawback of such prior-art weight-based systems has been the necessity of making mathematical calculations to determine collected volume and collection rate. Furthermore, it has been necessary to initially obtain the tare weight of the collection container prior to each collection procedure. Moreover, with such systems it has been necessary to reinitiate the collected volume and rate measurement procedures with each change of collection container. This is not only time consuming, but also introduces a potential for error in the volume and rate determinations.

The plasmapheresis system described herein incorporates a system which automatically determines and displays the volume of a blood fraction collected in plasmapheresis and similar blood fractionation apparatus by analyzing incremental changes in collected plasma weight over successive time intervals. The volume collected is continuously displayed, without consideration of changes in tare weights or changing of the plasma collection container. This system is described in detail in the application of Arnold C. Bilstad and John T. Foley, entitled "Blood Fractionation Apparatus Having Collected Volume Display System", Ser. No. 330,899, now U.S. Pat. No. 4,458,539, filed concurrently herewith and incorporated herein by reference.

It is also desirable in plasmapheresis and other blood fractionation procedures that the rate of collection of the blood component be continuously displayed. This allows the fractionation apparatus to be adjusted for optimum performance, and provides an additional safety check on the operation of the apparatus. In prior art filter-type plasmapheresis systems the collection rate could only be determined by mathematical analysis of collected volumes of plasma over known time intervals. This procedure required an undue amount of time on the part of an operator, and was by its nature often not a sufficiently current indication by which operating adjustments to the apparatus could be made.

The plasmapheresis apparatus described herein incorporates a system wherein plasma collection rate is derived by accumulating and averaging incremental changes in plasma volume, as developed by the previously described volume display system, and is displayed in a clear and unambiguous digital format, allowing the rate display to be used for adjustment of the plasmapheresis apparatus. This system is described in detail in the application of Arnold C. Bilstad and John T. Foley, entitled, "Blood Fractionation Apparatus Having Collection Rate Display System", Ser. No. 330,901, now U.S. Pat. No. 4,481,827, filed concurrently herewith and incorporated herein by reference.

In plasmapheresis procedures it is frequently desirable that a replacement fluid be introduced into the processed plasma-deficient blood to replace the collected plasma prior to returning the processed blood to the donor. In this exchange procedure the replacement fluid is typically introduced by a replacement pump at a fixed volume ratio to the collected plasma, as specified by the attending physician.

In prior art filter-type plasmapheresis systems the speed of the replacement pump, and hence the replacement fluid rate, was manually set by the operator, after observing the plasma collection rate and mathematically calculating the necessary replacement rate from the specified replacement ratio. For each change in collection rate is was necessary to manually reset the replacement rate, and failure to note a change in collection rate resulted in an improper replacement rate.

The present invention overcomes these drawbacks by providing a system which automatically proportions the volume of replacement fluid added to the volume of plasma actually collected according to an operator-set ratio. The system includes an autologous mode, wherein plasma is withdrawn from the collection bag by the replacement fluid pump for treatment and return to the donor at a rate which is automatically adjusted to maintain a constant volume of collected plasma in the collection container.

SUMMARY OF THE INVENTION

The invention is directed, in a blood fracionation apparatus for separating and collecting a blood fraction from whole blood, and of the type utilizing a flow system having a collection container for the collected component, and a motor driven replacement pump for adding replacement fluid to the fractionalized blood component, to a control system for maintaining a predetermined ratio between the volume of fraction collected and the volume of replacement fluid added. The system includes derivation means including an electrical transducer for producing a collection signal indicative of incremental units of volume of the fracion collected and means responsive to operation of the replacement fluid pump for providing output pulses indicative of the volume of replacement fluid added. A first ratio circuit responsive to the collecton signals produces a first comparison signal, and a second ratio circuit responsive to the replacement fluid output pulses produces a second comparison signal. Comparison means are provided for comparing the cumulative occurrences of the first comparison pulses with the cumulative occurrences of the second comparison pulses to develop an output signal for controlling the speed of the replacement pump motor.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 6 is a simplified block diagram of the collected volume display system of the plasmapheresis apparatus of FIGS. 1 and 2.

FIG. 7 is a logic table useful in understanding the operation of the collected volume display system of the plasmapheresis apparatus.

FIG. 8 is a depiction of certain hypothetical weight variations of the collection container with time useful in explaining the operation of the collected volume display system of FIG. 6.

DESCRIPTION OF THE PREFERRED EMBODIMENT

Figure 1:
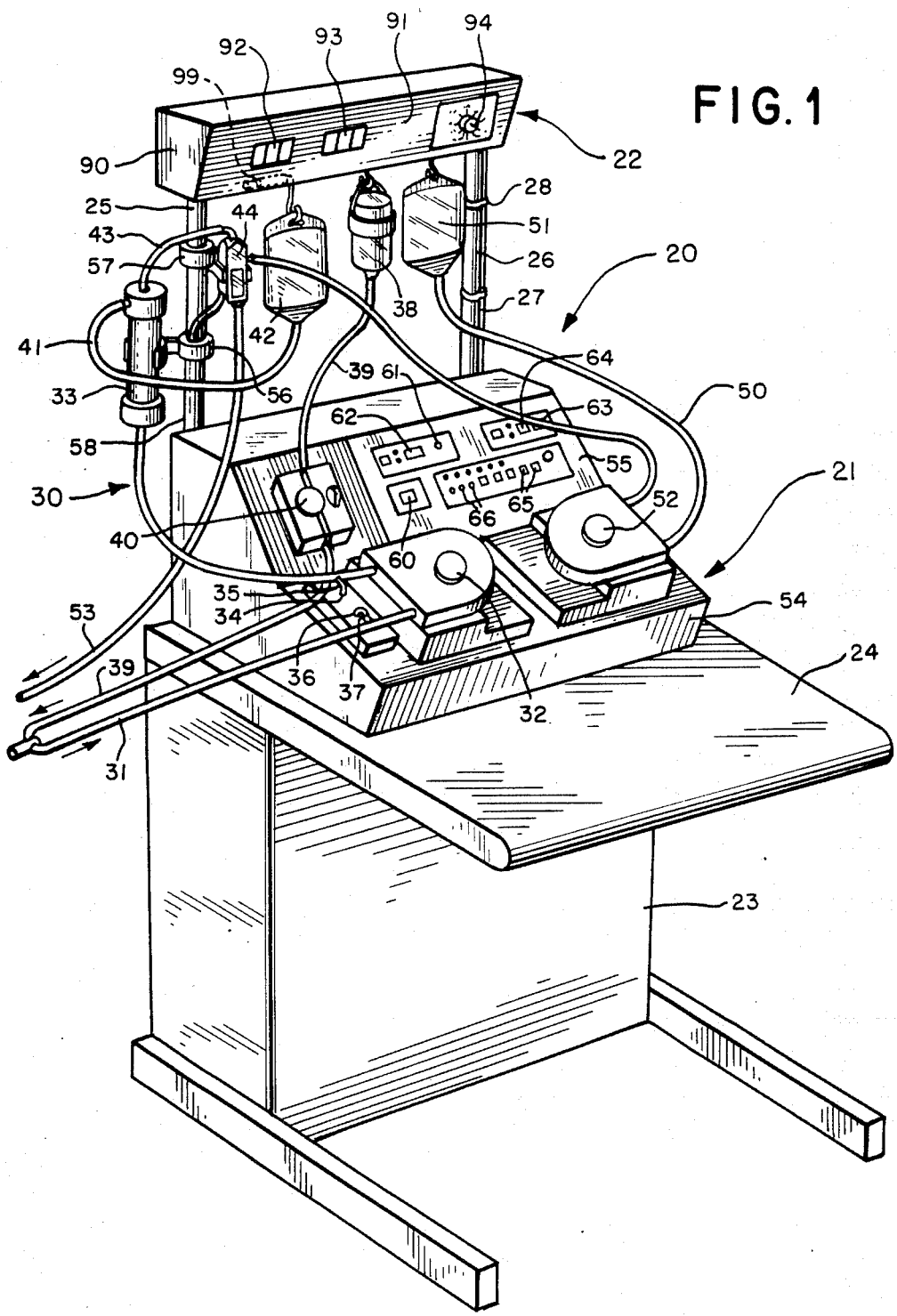
FIG. 1 is a perspective view of plasmapheresis apparatus incorporating a replacement fluid ratio control system constructed in accordance with the invention.

Referring to the drawings, and particularly to FIG. 1, a plasmapheresis apparatus 20 incorporating the present invention is seen to include a lower table-mounted processing unit 21, and an upper rack-supported collection monitor and reinfusion rate control unit 22. The processing unit is shown mounted on a table 23 of conventional design having a generally horizontal top surface 24 on which the processing unit is supported. However, the processing unit may be removed as necessary from table 23 and installed on other surfaces.

The collection monitor and reinfuse control unit 22 is preferably supported on a pair of vertical support poles 25 and 26 attached to the rear wall (not shown) of the processing unit. As shown in FIG. 1, the separation between the two units is preferably sufficient to allow a plurality of collection and dispensing containers of conventional construction to be hung by appropriate hangers from the bottom surface of the monitoring and control unit. Necessary electrical connections are established between the two units by means of an electrical cable 27 attached to support pole 26 by cable ties 28 or other appropriate fastening means.

Figure 2:
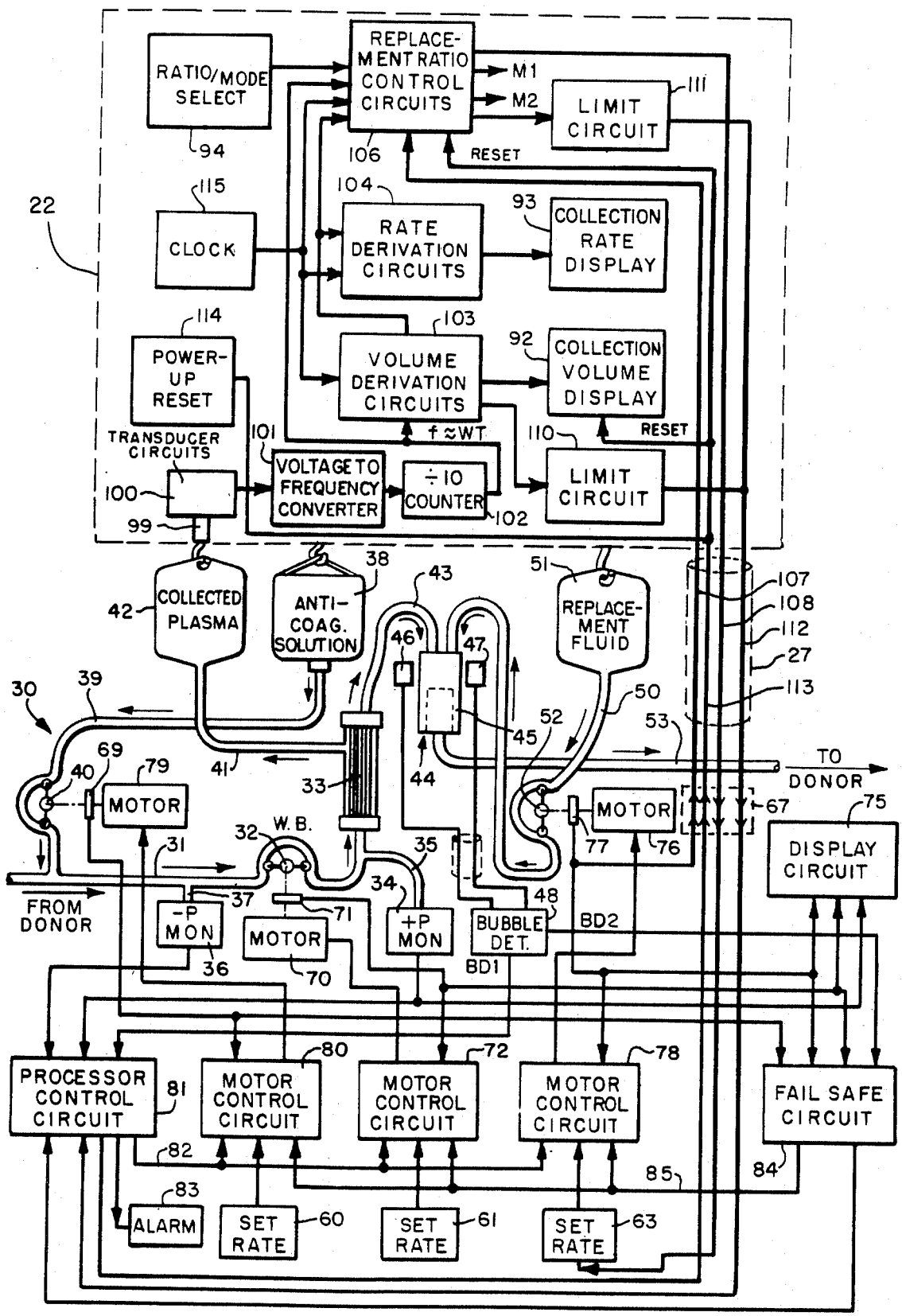
FIG. 2 is a functional block diagram showing the principal components of the plasmapheresis apparatus of FIG. 1.

The processing apparatus 20 is capable of operation in an exchange mode, wherein a desired blood component, such as plasma, is removed from whole blood received from a donor and replaced at an automatically maintained volume ratio by a replacement fluid added to the processed blood prior to the processed blood being returned to the donor; or in an autologous mode, wherein the collected component is automatically removed from the collection container so as to maintain a constant volume in the container, is processed in a secondary treatment system, and is then returned to the donor. A fluid circuit for use in the exchange mode is generally identified by the reference numeral 30 in FIG. 1 and shown schematically in FIG. 2. The fluid circuit 30 includes a plurality of flexible plastic tube segments which form fluid conduits between various components of the fluid circuit. As shown in FIG. 2, whole blood derived from a donor is conveyed through a first tubing segment 31 and a first peristaltic-type whole blood (WB) pump 32 to a hollow fiber-type filter 33 mounted on support rod 25. The operation of the WB pump is monitored by a positive pressure (+P) transducer monitor circuit 34 connected to tubing segment 31 downline of the WB pump by a tubing segment 35. Negative pressure, such as might occur upon the collapse of a vein, is monitored for by means of a negative pressure (−P) monitor circuit 36 connected to tubing segment 31 upline of the WB pump 32 by a tubing segment 37.

To prevent blood from clotting while in process in the apparatus anticoagulant solution from a supply container 38 is introduced at the point of blood withdrawal through a tubing segment 39. A peristaltic-type pump 40 is provided along tubing segment 39 to provide a controlled rate of addition of the anticoagulant fluid to the whole blood.

Plasma separated from the whole blood within the hollow fiber filter 33 is conveyed by a tubing segment 41 to a plasma collection container 42. The pressure provided by WB pump 32 is sufficient to cause flow from the filter to the collection container. The plasma-deficient processed blood from filter 33 is conveyed through a tubing segment 43 to an ultrasonic bubble detector 44, which may be similar in structure and operation to that described in the copending application of Arnold C. Bilstad and Michael Wicnienski, entitled, "Liquid Absence Detector", Ser. No. 127,552, filed Mar. 6, 1980. Basically, bubble detector 44 includes a hollow housing having an internal filter screen assembly 45. Any bubbles in the processed blood fluid collect at the upper portion of the housing. An ultrasonic sound transmitter 46 and an ultrasonic sound receiver 47 positioned at opposite sides of the upper portion of the housing detect bubble formation. The source 46 and detector 47 are connected to a dual bubble detector circuit 48 which provides first and second independent bubble detector (BD) outputs upon the occurrence of a bubble or liquid absence.

Replacement fluid is added to the plasma-deficient blood at this location through a tubing segment 50 which is connected at one end to a replacement fluid container 51 and at its other end to the housing of bubble detector 44. A peristaltic-type replacement pump 52 is positioned along tubing segment 50 to establish a controlled flow rate for the replacement fluid. The combined plasma-deficient whole blood and replacement fluid are pumped from bubble detector 44 back to the donor through a tubing segment 53.

As shown in FIG. 1, the processor unit 21 of plasmapheresis apparatus 20 is housed in a cabinet 54 which includes a sloped front upper portion on which a control panel 55 and the anticoagulant pump 40 are located. The cabinet also includes a sloped front lower portion on which the WB pump 32 and replacement pump 52 are mounted, together with the inlet to the positive pressure monitor 34 and the inlet to the negative pressure monitor 36. When flow system 30 is installed on the plasmapheresis apparatus, the anticoagulant container 38, replacement fluid supply container 51 and plasma collection container 42 are suspended from the overhead monitoring and control unit 22 as shown, and the hollow fiber filter 33 is mounted by means of an appropriate mounting bracket 56 to vertical support rod 25. Bubble detector 44 is similarly mounted to support rod 25 by means of a mounting bracket 57, and the ultrasonic source 46 and detector 47 thereof are electrically connected to processor unit 21 by an electrical cable 58.

Control panel 55 includes operator-actuated controls for operating the plasmapheresis apparatus. These include a selector switch 60 by which the operating speed of the anticoagulant pump 40 is set, a potentiometer control 61 and digital readout 62 by which the operating speed of the WB pump 32 is controlled, and a potentiometer 63 and digital readout 64, by which the operating speed of the replacement pump 52 is controlled. A plurality of pushbutton switches 65 are provided to establish the operating mode of the apparatus, and a plurality of status-indicating lights 66 provide indications of malfunctions in the system.

The processor unit 21 in conjunction with flow circuit 30 constitutes a complete plasmapheresis system which may be operated without monitor and control unit 22. Utilized in this manner, the construction and operation of the apparatus is as described in detail in the previously identified application of Arnold C. Bilstad and John T. Foley entitled, "Blood Fractionation Apparatus", filed concurrently herewith. Thus operated, the system includes no provision for directly indicating the total volume of plasma actually collected or the rate of plasma collection, and no capability for automatically operating the reinfusion pump to maintain a desired volume ratio with plasma collected in the plasma collection container. Instead, during reinfusion the reinfusion rate is calculated from the volume of plasma collected over a known time period, and the result is manually set by means of control 63 and readout 64. The collection monitor and reinfusion control unit of the invention can be easily added at any time by merely plugging cable 27 into a connector 67 (FIG. 2) provided on the processor unit 21.

Basically, within the processor unit 21, the WB pump 32 is driven by a motor 70 having a mechanically coupled tachometer 71. Power for operating motor 70 is provided by a motor control circuit 72 which responds to rate setting means in the form of potentiometer control 61 and a feedback signal from tachometer 71 to maintain a desired motor operating speed. The actual pump flow rate is displayed by readout 62 as part of a display circuit 75, which receives the output signal from tachometer 71.

Similarly, the replacement pump 52 is driven by a motor 76 having an associated tachometer 77. Power for motor 76 is provided by a motor control circuit 78 which responds to a feedback signal from tachometer 77 and the rate selected by the panel-mounted potentiometer 63 to maintain a desired constant motor speed.

The actual pump flow rate is displayed by readout 64 as part of the display circuit 75.

The anticoagulant pump 40 is driven by a stepper motor 79 having an associated tachometer 69. Drive signals for motor 79 are developed by a motor control circuit 80 which responds to rate selection switch 60 to maintain a desired constant anticoagulant flow rate.

The operation of the various pump motors is controlled by a processor control circuit 81 which includes mode select pushbuttons 65 on front panel 55. System malfunctions, such as negative pressure at pressure monitor 36, or excessive positive pressure at pressure monitor 34, or the occurrence of a bubble or other fluid absence as signaled at the first output (BD1) of the dual bubble detector circuit 48, result in the application of an appropriate signal to the processor control circuit 81. This circuit responds by producing a control signal on a first motor control line 82 for application to the pump motor control circuits 72, 78 and 80 to interrupt operation of the motors. In addition, an alarm 83 associated with the processor control circuit 81 may be sounded and an appropriate one of indicator lamps 66 may be lit to alert the operator.

The processor unit 21 further includes a failsafe circuit 84 which functions to remove power from the pump motors in the event that processor control circuit 81 fails to respond to a system malfunction. To this end, the outputs of motor tachs 69, 71 and 77 are applied to the failsafe circuit, together with the second output (BD2) of bubble detector circuit 48. Upon the occurrence of a bubble or fluid absence, as signaled by bubble detector circuit 48, failsafe circuit 84 determines from the simultaneously applied tachometer output signals whether the pump motors have in fact stopped and, if motion is detected after a period of time, provides an additional stop signal which removes motor operating power to motor control circuits 72, 78 and 80 on a second motor control line 85.

As shown in FIG. 1, the collection monitor and replacement fluid ratio control unit 22 of plasmapheresis apparatus 20 includes a housing 90 which extends between the vertical mounting posts 25 and 26 at a height sufficient to allow the various collection and supply containers 38, 42 and 51 to be suspended underneath. The housing includes a downwardly inclined front panel 91 on which a first digital readout 92 is mounted for indicating the volume of plasma collected, and a second digital readout 93 is mounted for indicating the rate of plasma collection. A selector switch 94 allows the user to condition monitor and control unit 22 to provide a desired replacement ratio in the exchange mode, or to select the autologous mode, in which, with an appropriate flow system, a fixed volume of collected plasma is maintained in collection container 42 as plasma is withdrawn, processed and returned to the donor.

As shown in FIG. 2, the collection monitor and reinfuse control unit 22 of apparatus 20 includes a strain-gauge transducer 99 from which the plasma collection container 42 is suspended. The transducer is incorporated in a circuit 100 which develops an analog output signal having a voltage level dependent on the weight of collection container 42 and the collected plasma therein. The transducer output signal is applied to a voltage-to-frequency converter 101 which develops a variable frequency weight-indicative output signal. This signal is applied to a divide-by-ten counter 102. The counter output is applied to volume derivation circuits 103, wherein frequency variations over successive time intervals are analyzed and stored in accordance with the invention to develop a cumulative volume collected signal. This signal is applied to volume display 62, which provides a digital display of plasma volume collected.

Volume derivation circuits 103 also produce collection pulses indicative of each incremental amount or unit of plasma collected. This pulses are applied to rate derivation circuits 104 wherein they are accumulated over a time period to obtain an output signal indicative of the plasma collection rate. This signal is applied to rate display 64, which provides a digital display of the plasma collection rate.

The volume collection pulses are also applied to replacement ratio control circuits 106. These circuits compare the number of collection pulses, representing the volume of plasma collected, with replacement motor tachometer pulses conveyed from processor unit 21 over a line 107, representing the volume of replacement fluid replaced, and develop an appropriate analog speed control signal for application to the replacement motor control circuits 78 over a line 108. An operator-selected ratio set by switch 94 is automatically maintained by the ratio circuits.

In the event that volume derivation circuits 103 or ratio control circuits 106 detect an over-limit condition in their processing circuits, respective over-limit circuits 110 and 111 provide an over-limit alarm signal on a line 112 for application to control circuit 81 of the processor unit.

Reset of volume display 62 and ratio control circuits 106 when processor 21 is in the prime mode is accomplished by a reset line 113. Reset is also accomplished during initial power-up of the apparatus by a conventional power-up reset circuit 114 connected to reset line 113. Timing pulses required for the various circuits of unit 22 are provided by a clock circuit 115 within the unit. Basically, this clock circuit provides MEASURE and $\overline{\text{MEASURE}}$ clock pulses which establish measurement intervals, during which certain measurement functions are accomplished, and compute intervals, during which certain signal analysis and data transfer functions are accomplished; and a series of clock pulses $T_1$-$T_4$, which sequence the data processing functions during the compute period.

Figure 3:
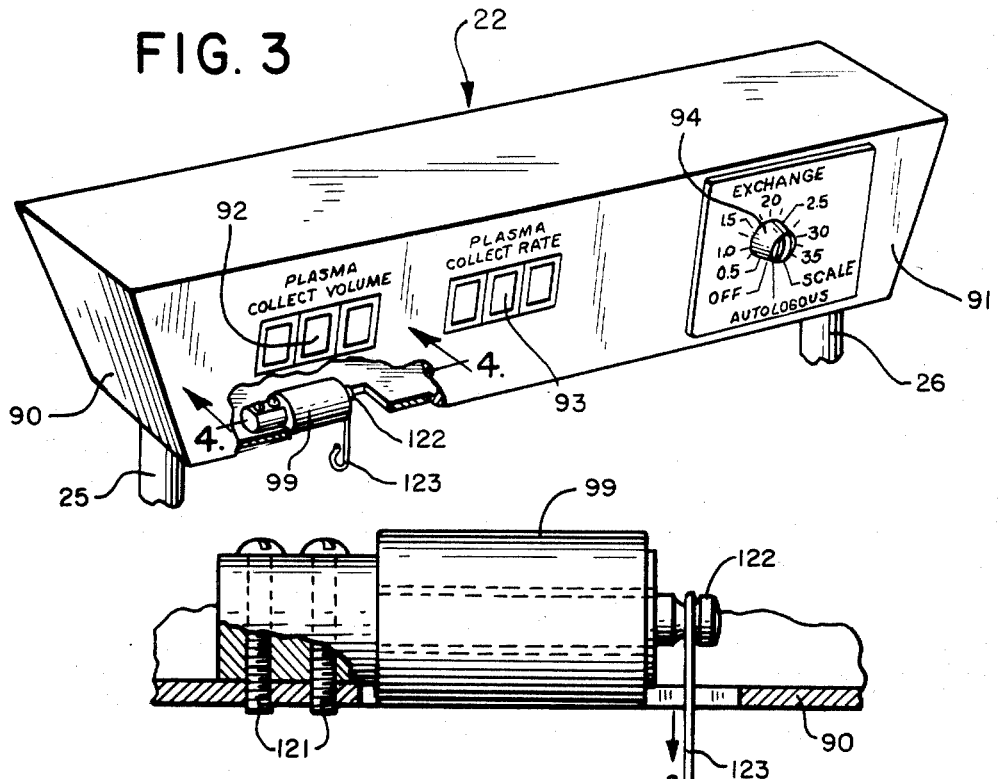
FIG. 3 is an enlarged perspective view of the overhead collection monitor and replacement rate control unit of the plasmapheresis apparatus of FIG. 1 partially broken away to show the electrical strain transducer incorporated therein.
Figure 4:
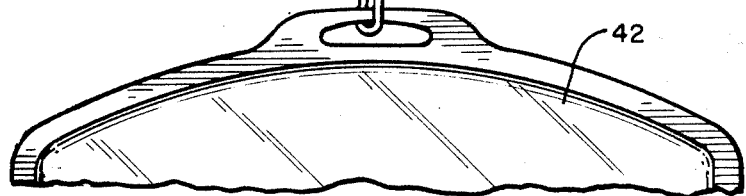
FIG. 4 is an enlarged side elevational view partially in section of the electrical strain transducer in conjunction with a plasma collection container.

Referring to FIGS. 3 and 4, the electrical strain-gauge transducer 99 is mounted to the bottom of housing 90 by machine screws 121 or other appropriate mounting means. This transducer, which may be conventional in construction and operation, includes at its unsupported end a protruding sense pin 122 from which the plasma collection bag 42 is suspended by means of a clip 123 or other appropriate means.

Figure 5:
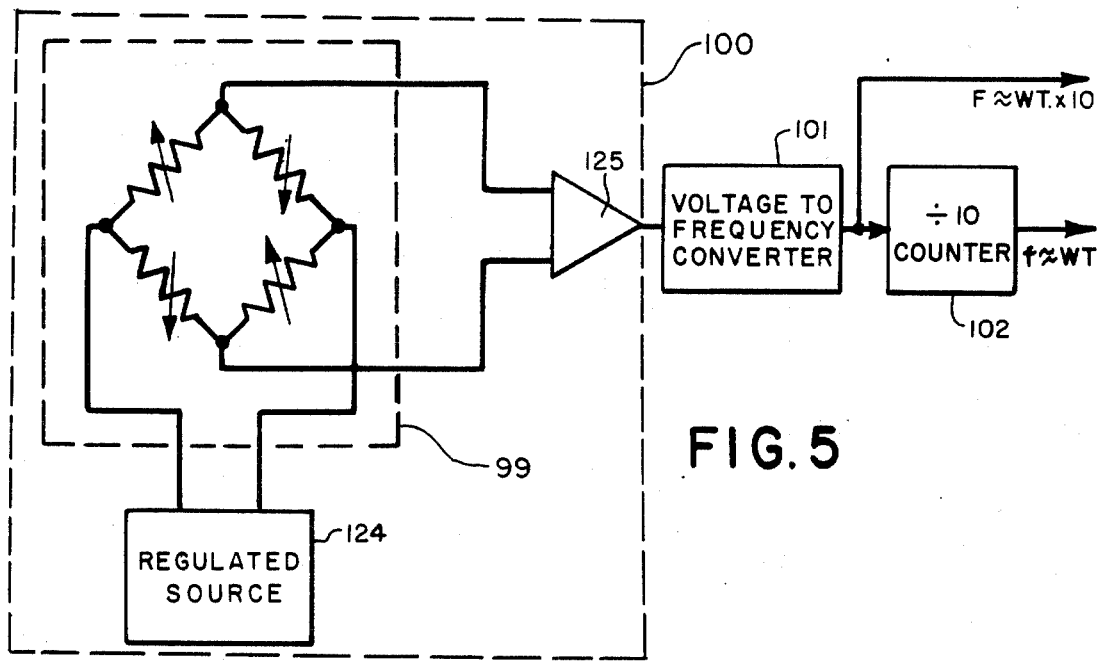
FIG. 5 is a simplified schematic diagram of the circuitry utilized in conjunction with the electrical strain transducer.

As shown in FIG. 5, transducer 99 provides a conventional resistance bridge circuit having an output resistance dependent on the force exerted on sense pin 122. A regulated voltage source 124 is connected to the input terminals of the bridge network, and the output terminals of the network are connected to a differential amplifier 125 in accordance with conventional practice. The output of amplifier 125, which constitutes an analog voltage amplitude dependent on the strain exerted on the transducer, is applied to voltage-to-frequency converter 101. This circuit generates an output signal which has a frequency proportional to the applied analog voltage, and hence to the downward force (or weight) exerted on sense pin 122 of the transducer.

In practice, transducer circuit 100 may be designed in accordance with conventional and well known techniques to provide in conjunction with converter 101 an output signal having a 10 hertz variation in output frequency for each milliliter of plasma collected in plasma collection container 42, and various conventional compensating and offset circuits (not shown in FIG. 5) may be incorporated in the circuitry associated with transducer 99 to obtain a more linear and temperature independent output. Typically, for an offset voltage of one volt at the input of differential amplifier 125, a base frequency of 10,000 hertz may be realized at the output of converter 101.

Referring to FIG. 6, the output signal from voltage-to-frequency converter 101 is applied to frequency divider 102, which divides the 10,000 hertz signal to develop a 1,000 hertz pulse signal having a deviation of 1 hertz per milliliter of plasma collected.

Within volume derivation circuits 103 the 1,000 hertz variable-frequency signal is periodically applied during measurement intervals of fixed time duration to an input counter 130, which counts the pulses during each measurement interval to develop an output signal at the end of each measurement interval indicative of the pulse frequency during the interval. In the illustrated plasmapheresis apparatus, the measurement intervals are obtained by application of a MEASURE clock pulse developed by clock 115 to the inhibit input of frequency divider 102, which has the effect of enabling the divider, and hence counter 130, during the measure intervals.

By selecting a measurement interval of one second, the counter output at the end of the measurement interval is made to equal the frequency of the transducer signal in hertz. However, other measurement intervals may be selected if appropriate.

Following each measurement interval, the counter output is added in an A+B binary adder 131 with a previous inverted output of the counter, as stored in a latch register 132. Consequently, the output of the binary adder is a difference signal representative of the difference between the two counter outputs. If the difference between the counter outputs represents a collection increment which is physically possible by processor unit 21 in the selected measurement interval (in the present embodiment either 0, 1, 2 or 3 collection units within a one second interval), as determined by logic circuitry within control circuits 133, then the output of the binary adder 131 is converted upon the occurrence of a $T_2$ (latch) clock signal to a serial signal consisting of either 0, 1, 2 or 3 collection pulses within a parallel-to-serial converter 134. These collection pulses are applied to a display counter 135 through an AND gate 136, and to an output line 137 for application to utilization means such as rate deviation circuits 104 and rate control circuits 106 of the apparatus. Display counter 135 periodically displays the accumulated count upon receipt of a $T_2$ (latch) clock pulse.

Display counter 135 accumulates the applied pulses for the duration of each plasmapheresis procedure. By adapting the voltage-to-frequency converter 102 to provide a 1 hertz deviation in frequency for the equivalent weight of each milliliter of plasma collected, the accumulated count in counter 135 may be read out directly on the digital volume collected display 62 as milliliters of plasma collected. Display counter 135 is reset only upon completion of the plasmapheresis procedure by a total volume reset pulse on reset line 113.

Counter 130 is periodically reset following each measurement interval by a $T_4$ (reset) clock pulse.

If the output of binary adder 131 is greater than 3 units, representing the physical impossibility in the illustrated plasmapheresis system of more than 3 milliliters of plasma being collected in one second, or of more than 180 milliliters being collected in one minute, then the difference is considered invalid by control circuits 133 as having been caused by a physical disturbance to the collection container and no increment is added to display counter 135. Also, when the output of binary adder 131 is negative, as indicated by the absence of an appropriate carry output on carry line 138, corresponding to a loss of plasma impossible in the system, the differential is considered invalid and no increment is added.

To provide a meaningful reference from which to measure the differential, register 132 is latched by $T_3$ (load) clock pulses applied through an AND gate 139 to assume the existing reading of counter 130 after the differential output of binary adder 131 has been analyzed and, if valid, incremented to counter 135. This is done in all instances, except if the differential output of binary adder 131 is negative and less than 3 milliliters. In this case register 132 is not latched and therefore retains the previous count of counter 130, and the subsequent deviation is taken from the stored count. This precludes slight flow irregularities such as might result during normal operation of the apparatus from affecting the count.

Additional protection is provided against physical disturbances to the collection container by circuitry in control circuits 133 which causes the differential output of binary adder 131 to be taken as invalid, and register 132 to not be latched for four measurement intervals, following a differential output from binary adder 131 greater than 3. This prevents small transient disturbances to the collection container or flow system, such as might occur for a period of time following a large disturbance to the flow system or apparatus, or following a change of collection containers, from affecting the accuracy of the collected volume display and the collection pulses prodoced by the flow system.

The operation of the volume derivation system is tabulated for a system having a maximum collection rate of 3 milliliters per second as rules I–IV in FIG. 7. If V is taken as plasma volume (based on weight) in a 1 second interval, and $\Delta V$ as the change in volume (based on weight) between successive one second intervals, then it is seen that only those positive volume changes which are either 1, 2, or 3 milliliters in the one second interval, and therefore fall under rule II, are recognized as valid collection increments to be applied to display counter 135. This is illustrated in FIG. 8 by a hypothetical plot of plasma volume (based on weight) over time intervals $t_0$–$t_{13}$. At an initial time $t_0$ the A and B inputs to binary adder 131 are both identical. Consequently, according to rule III of FIG. 7 the differential output A-B is 0, an increment of 0 is produced, and the collected volume count in counter 135 is 0. At time $t_1$, the immediately preceding count is applied to input A, and the next preceding count is applied by register 132 to input B. The resulting A-B differential signal is +1, and in accordance with rule II a 1 milliliter increment is produced for application to display counter 135, resulting in a cumulative count in that counter of 1.

At time $t_2$ the B input of binary adder 131 is a binary one contained in register 132, and the A input is a binary four from counter 130. The +3 differential results in three pulses being incremented to display counter 135, causing the counter to assume a counting state of 4. Examination of the curve of FIG. 8 at this time will show that in fact four units of plasma have been collected.

At time $t_3$ register 132 has assumed the four count of counter 130 at the end of the previous measurement interval. Input counter 130 now reads 8, making the differential output of adder 131 a +4. In accordance with rule I of FIG. 7, this results in a 0 increment being supplied to display counter 135. Since the deviation exceeded 3, a four period delay is initiated before binary adder 131 can increment counter 135.

After the four period delay under rule 1, any transient disturbances will have dissipated, and the system resumes analyzing received data at time $t_7$. From time $t_7$ to time $t_8$, the indicated volume falls to four units, producing a differential of −4. Under rule IV, a zero is incremented to display counter 135 and another four second delay period $t_8$–$t_{11}$ is initiated. At time $t_{12}$, a differential of −2 is realized. Under rule III this results in no incremental output and no change in the cumulative plasma collection count, which remains at +4 units. However, register 132 is caused to retain its four count from time $t_8$ until time $t_{13}$. At time $t_{13}$ however, a +1 increase is recognized by binary adder 131. This causes an increment of one pulse to be applied to display counter 135, and the resulting count in that register to be 5 units of volume. This volume is displayed by the total volume display 62.

By comparing the collected volume of plasma at time $t_0$ with that at time $t_{13}$, it is seen that 5 units of plasma have in fact been collected. Those large positive or negative excursions (in excess of three milliliters in the illustrated apparatus) are considered by the system as not resulting from plasma collection, but from the application of external forces to the transducer, as when changing the plasma collection container, and are accordingly ignored in computing total volume collected. Similarly, since a negative collection rate is physically impossible, small negative excursions of less than 3 milliliters are viewed by the system as chance events which even themselves out with time, and are therefore not accumulated.

Figure 9:
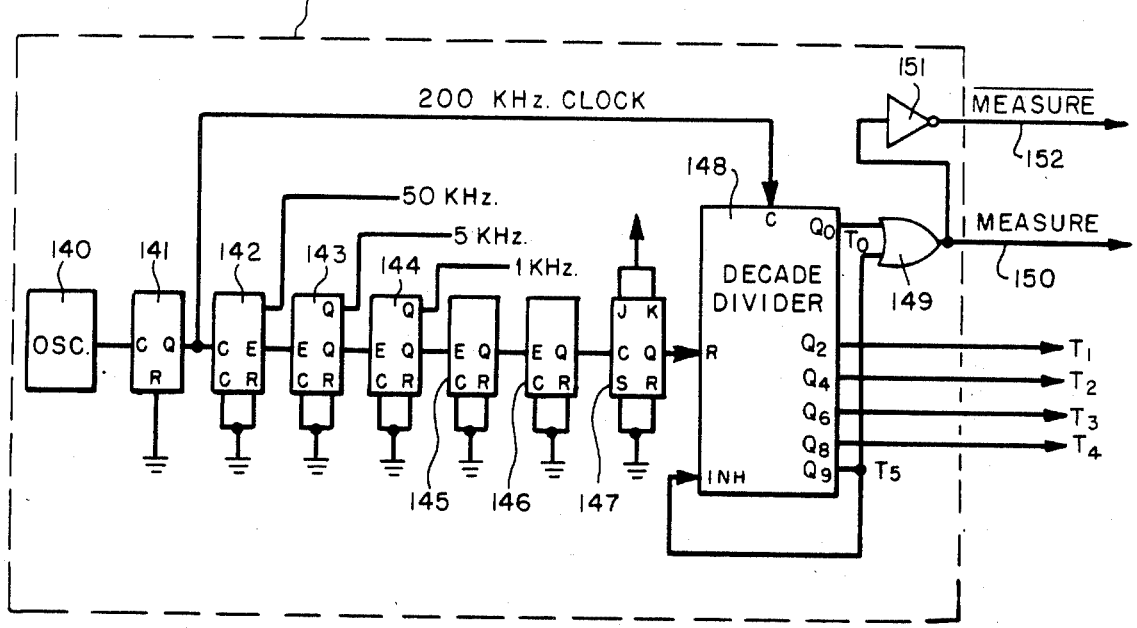
FIG. 9 is a simplified schematic diagram of the clock circuit of the plasmapheresis monitor and control unit of FIGS. 1 and 2.

Referring to FIG. 9, the clock pulses required for operating the various circuits of the collection monitor and reinfuse control unit 22 are supplied by an oscillator 140, six decade counters 141–146, and one flip-flop 147 within clock circuits 115. Counters 141–146 are connected to oscillator 140 in a conventional manner to obtain 200 kHz, 50 kHz, 5 kHZ, 1 kHz and 1 Hz clock pulses. The 1 Hz clock pulses and the 200 kHz clock pulses are applied to the reset and clock inputs, respectively, of a decade divider 148. This divider functions as a Johnson counter to produce a series of output pulses $T_1$–$T_4$ following each reset pulse from flip-flop 147. Since the clock pulses applied to the divider are at a relatively high frequency, the sequence of pulses $T_1$–$T_4$ is generated by the divider within a short time interval.

After the divider has completed the pulse sequence $T_1$–$T_4$, an output $T_5$ is generated. This output is applied to the inhibit input of the divider to prevent further counting, and to one input of an OR gate 149. The other input of OR gate 149 receives a $T_0$ output from the divider, causing the gate to produce a MEASURE control signal on a line 150 whenever the divider is reset and not counting. An inverter 151 connected to the output of OR gate 149 produces a $\overline{\text{MEASURE}}$ control signal on a line 152.

Figure 10:
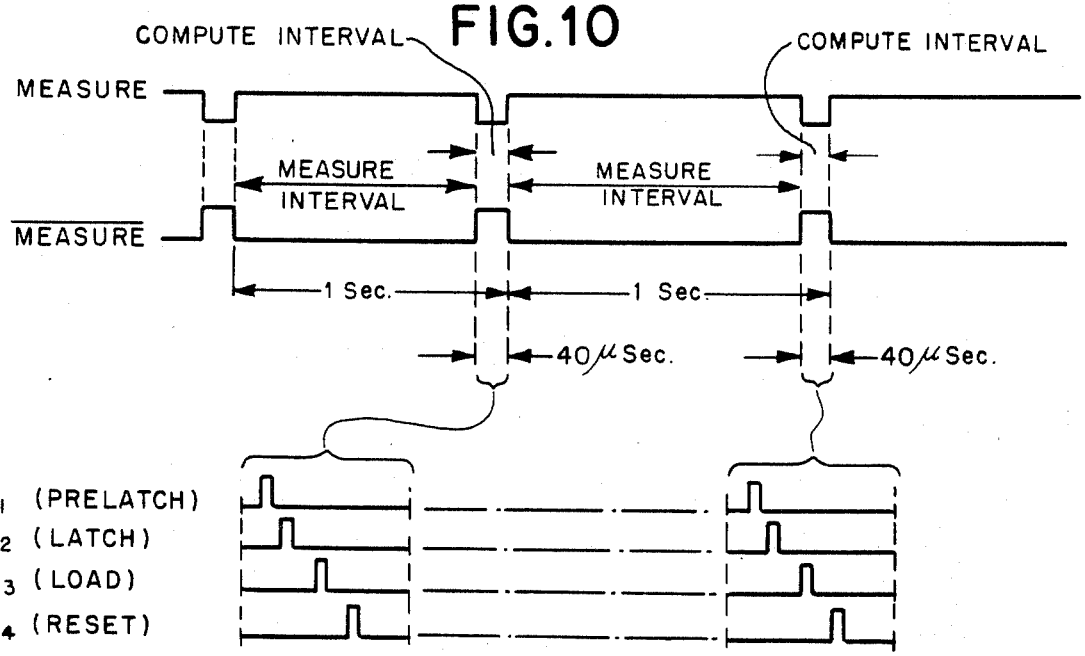
FIG. 10 is a depiction of certain waveforms produced by the clock circuit of FIG. 9 useful in understanding the operation of the collected volume and collection rate display systems of the apparatus.

As illustrated in FIG. 10, the MEASURE control signal developed by decade divider 148 provides the 1 second measurement period during which counter 130 counts pulses from divider 127. Following each such measure interval, upon application of a reset pulse to decade divider 148, a 40 microsecond computing period occurs while divider 148 counts through its cycle. Clock pulses $T_1$–$T_4$, which are associated with prelatch, latch, load and reset functions, respectively, of circuits 103, 104 and 106, occur during this compute period. Since clock pulses $T_1$–$T_4$ are obtained at alternate outputs of divider 148, a time space exists between the clock pulses which precludes any overlap in the functions they control.

Figure 11:
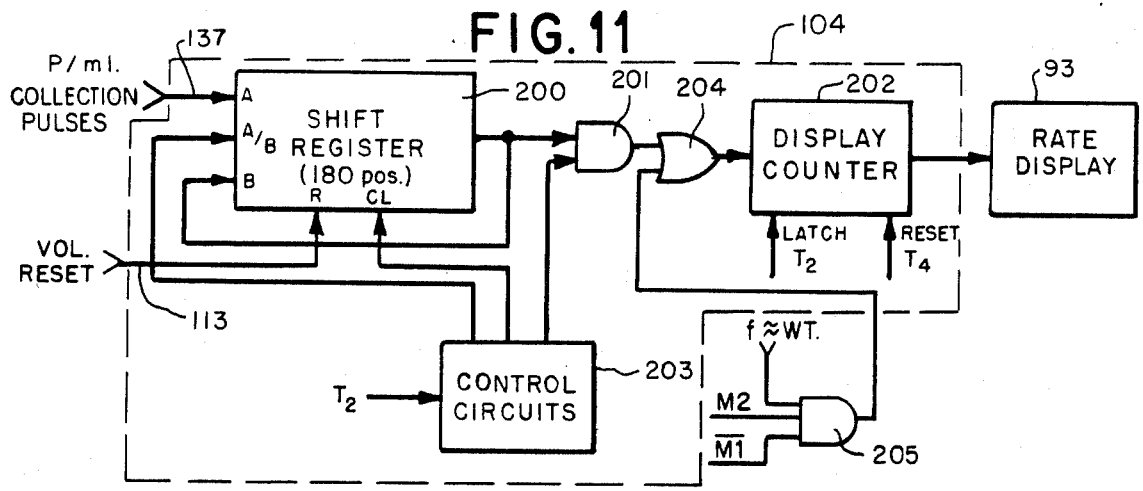
FIG. 11 is a functional block diagram of the collection rate display system of the plasmapheresis system of FIGS. 1 and 2.

The plasma collection pulses developed by volume derivation circuits 103 are utilized by collection rate derivation circuit 104 to develop a display of plasma collection rate. This circuit, which is described in detail in the copending application of Arnold C. Bilstad and John T. Foley entitled, "Blood Fractionation Apparatus Having Collection Rate Display System", filed concurrently herewith, includes a shift register 200 (see FIG. 11) for receiving the plasma collection pulses. This register has data positions for storing the serial data received from volume derivation circuits 103 over sixty preceding one second measurement intervals. Since in the illustrated plasmapheresis apparatus each measurement interval results in the production of either zero, one, two or three one milliliter collection pulses, or data bits, three data positions are reserved in the register for each of the sixty measurement intervals to be taken into account. Thus, 180 data positions are provided in register 200.

When the three data bits for each measurement interval have been entered into register 200 for the preceding 60 intervals, the register contains a count total equal to the total number of milliliters of plasma collected over the preceding 60 intervals. If each interval is one second in duration, then the counting state of the register represents the number of milliliters collected in the preceding minute, which may be read as the collection rate in milliliters per minute.

The operation of shift register 200 is conventional in that the addition of each new bit of data at its input results in the overflow of one bit of data at its output. Thus, if three data bits are loaded at its input, three data bits are produced at its output. Since the data bits advance from input to output, the most recent data is located at the input of the register, and the oldest data is located at the output of the register. Consequently, when three data bits are entered representing the most recent data in a 60 second, or one minute, analysis period, the three data bits produced at the output represent data occurring before the analysis period. Thus, only collections in the previous minute are recorded in shift register 200.

To provide a display of the rate of plasma collection, the data bits contained in shift register 200 are periodically applied through appropriate switching means such as an AND gate 201 to a display counter 202. To this end, clock pulses are applied to shift register 200 to cause data within the register to appear serially at the output of the register. With AND gate 201 enabled, this data is applied to display counter 202, wherein the total number of collection pulses in the data is accumulated as a count representative of the number of milliliters of plasma having been collected in the preceding analysis period. The total count developed by counter 202 is displayed by collection rate readout 93 in milliliters of plasma collected per minute.

Shift register 200 has A and B inputs selected by application of a signal to its A/B select input. To update the rate display to reflect changes in flow rate, new data consisting of three bits for a new measurement interval is applied to the A input of shift register 200. Control circuits 203 enable the A input and apply appropriately timed clock pulses. The oldest three data bits in the register appear serially at the register output as the new bits are entered. Control circuits 203 inhibit AND gate 201 at this time to prevent the three oldest bits from being applied to display counter 202. Since the B input of the shift register is inoperative (not selected), the bits are not recirculated back into the register and cease to exist.

After the three new data bits have been applied to the A input, control circuits 203 cause the B input to be selected and AND gate 201 to be enabled. Clock pulses now applied to shift register 200 recirculate all 180 data bits in the register from the output back to the B input. At the same time, the same 180 data bits are applied through the enabled AND gate 201 to display counter 202, which has been reset by a $T_4$ (reset) clock pulse prior to the loading operation. After the 180 data bits in the register have completely recirculated, the application of clock pulses to the register is terminated, AND gate 201 is inhibited, and a $T_2$ (latch) clock pulse is applied to display counter 202 to cause that counter to display the count of the pulses just applied. Digital display 93 displays this count to the operator as milliliters of plasma collected per minute.

At the completion of the next measurement cycle a new set of collection data is produced by volume derivation circuits 103. Prior to receiving this data, control circuits 203 condition the A input of shift register 200 operative and inhibit AND gate 201. Then, after the new data has been received, display counter 202 is latched, AND gate 201 is enabled, and an additional 180 clock pulses are applied to shift register 200 to transfer the new data to counter 202 to begin the cycle anew.

Figure 12:
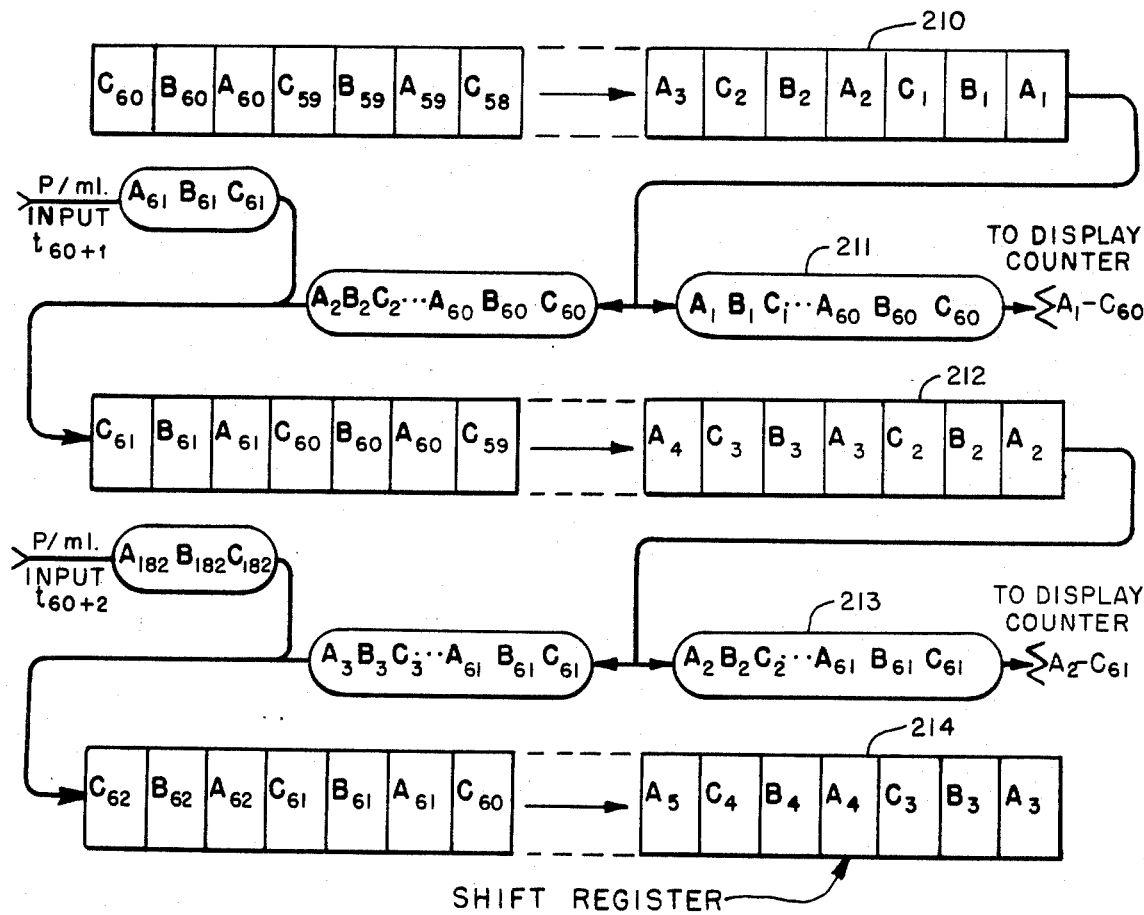
FIG. 12 is a depiction of hypothetical data flow useful in understanding the operation of the collection rate display system of FIG. 11.

Referring to FIG. 12, if each measurement interval is considered as having three data positions designated A, B and C, then after an initial 60 intervals shift register 200 may appear as shown by data group 210. If 180 clock pulses are now applied to the shift register an output data group 211 comprising data bits $A_1$ through $C_{160}$ will be applied to display counter 202. Subsequently, if new data $A_{61}$, $B_{61}$ and $C_{61}$ is introduced into the register, the $A_1$, $B_1$ and $C_1$ data is lost and the register contains data as shown by data block 212. This data is read to display counter as $A_2$–$C_{61}$ as shown by data block 213. If a third set of data comprising $A_{62}$–$C_{62}$ is entered, then the next oldest data $A_2$–$C_2$ is dropped, and the shift register assumes the data state shown by data block 214.

Figures 13, 14:
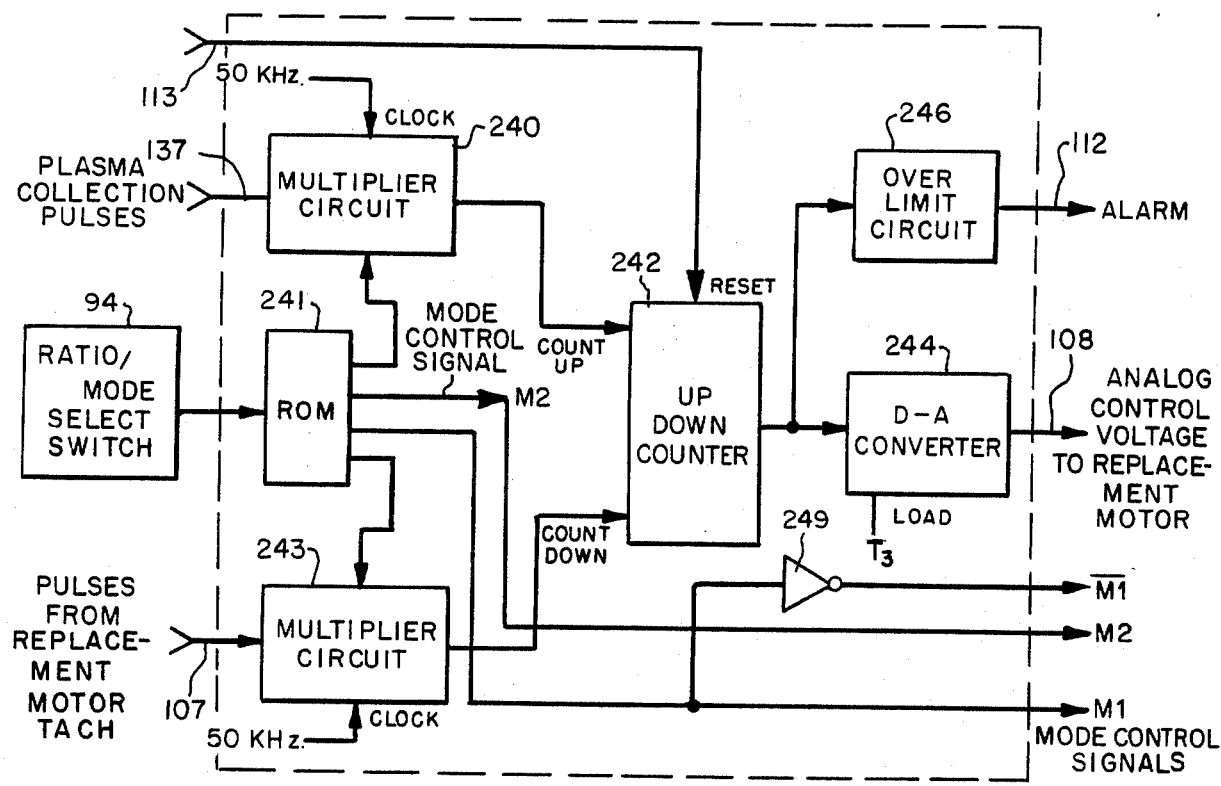
FIG. 13 is a simplified functional block diagram of the fluid replacement ratio control system of the plasmapheresis apparatus of FIGS. 1 and 2 configured in an exchange mode.
FIG. 14 is a tabulation of certain signals associated with the operation of the fluid replacement control system.

In accordance with the invention, the collection pulses developed by the volume derivation circuits 103 of the invention are utilized by ratio control circuits 106 to automatically control the rate at which collected plasma is replaced, and to provide an autologous mode wherein collected plasma can be treated and returned to the donor. Basically, as shown in FIG. 13, this system includes a rate multiplier circuit 240 to which the 1 milliliter collection pulses developed on line 137 by volume derivation circuits 103 are applied. Rate multiplier circuit 240 provides, in accordance with conventional practice, a selected number of pulses for each applied collection pulse. The number of pulses provided is dependent on an applied binary control signal developed within a read-only-memory (ROM) 241. The magnitude of the binary control signal, and hence the multiplication factor of the rate multiplier circuit 240, is dependent on an input signal applied to ROM 241 by the ratio/mode select switch 94. The output of rate multiplier circuit 240 is applied to the up count input of an up-down counter 242.

Within replacement ratio control circuits 106 the tachometer output pulses from replacement motor tachometer 77 are applied to a second rate multiplier circuit 243. The multiplication factor applied by this rate multiplier circuit is also dependent on an applied binary control signal developed by ROM 241, which is in turn also dependent on the ratio selected by the ratio/mode select switch 94. Thus, for a particular selected ratio, a predetermined number of output pulses will be produced by rate multiplier circuit 243 for each tachometer pulse received from tachometer 77. The output of rate multiplier circuit 243 is applied to the down count input of up-down counter 242.

With rate multiplier circuits 240 and 243 thus connected, the up-down counter 242 counts a predetermined number of counts in an up direction for each increment of plasma volume (weight) collected, and a predetermined number of counts in a down direction for each pulse received from the replacement pump motor tachometer. The counting state of the up-down counter 242 is indicated by a binary output signal. This signal is applied to a digital-to-analog converter 244 which converts the applied binary signal to an analog control voltage. This control voltage is applied by means of control line 108 to the rate determining circuit 63 of replacement pump motor 76.

In operation, as plasma is collected in plasma collection container 42 transducer conversion circuits 101 produce output pulses at a frequency dependent on the weight of the collected plasma. Within volume derivation circuits 103 these weight-related transducer signals are converted to an output signal providing one pulse per milliliter of plasma collected. These plasma collection pulses are applied within replacement ratio control circuits 106 to rate multiplier circuit 240, which provides a predetermined number of pulses to up-down counter 242 for each applied collection pulse, depending on the multiplication factor set by ROM 241. This causes up-down counter 242 to count up to successively higher counting states. Digital to analog converter 244 responds by generating an analog control voltage which increases in level with the increasing count. This control voltage causes motor control circuit 78 to energize motor 76 so as to pump replacement fluid into the flow system.

As motor 76 turns tach 77 provides output pulses which are carried on tach line 107 to rate multiplier circuit 243. In multiplier circuit 243 a multiplication factor is introduced dependent on the applied control signal from ROM 241. The resulting rate-multiplied pulses are applied to the down count input of up-down 242. These pulses cause that counter to count down, thereby tending to reduce the analog control voltage developed by digital-to-analog converter 244. Thus, a closed loop system is formed which functions to maintain a continuous count of plasma collected less replacement fluid infused, thereby tending to keep up-down counter 242 at a zero counting state.

By varying the multiplication factors of rate multiplier circuits 240 and 243 it is possible to maintain a predetermined volume ratio between plasma collected and replacement fluid added. Referring to FIG. 14, the factor set by rate multiplier circuit 240 may be considered the numerator, and the factor applied by rate multiplier circuit 243 may be taken as the denominator of the ratio maintained by the system. The necessary multiplication factors are set by ROM 241 in response to volume ratio selected by switch 94. For example, if a 1:0 ratio is selected, both rate multiplier circuits are set for a multiplication factor of 4 and up-down counter 242 receives four pulses for each increment of plasma collected and four pulses for each increment of fluid replaced. If a ratio of 0.5 is set, then rate multiplier circuit 243 is set for a factor of 4, and rate multiplier circuit 240 is set for a factor of 2. If a ratio of 2.0 is to be maintained, then rate multiplier circuit 243 is set to a factor of 4, and rate multiplier circuit 240 is set for a factor of 8. In this way, a range of ratios from 0.5 to 3.5 is obtained in the illustrated plasmapheresis apparatus by the replacement rate control circuit 106.

To prevent operation of the plasmapheresis apparatus in the event that the reinfuse pump is unable to maintain the desired ratio, such as might occur were it to stall, the control circuit includes an overlimit circuit 246 which monitors the output of up-down counter 242 and provides an alarm output in the event the counter exceeds a predetermined maximum count. The alarm signal is conveyed over lead 112 through cable 27 for application to processor control circuit 81 to terminate operation of the plasmapheresis apparatus.

Since the operation of up-down counter 242 continues over continuous sampling periods, the counter is not reset following each measurement interval. Instead, the counter is reset only upon a total volume reset, as when changing operating modes or upon initial power-up of the apparatus. Reset line 113 provides the necessary reset signal from the plasmapheresis apparatus through conductor 27.

An additional function of ROM 241 is to set the operating mode of the plasmapheresis monitor and control unit 22. To this end, ROM 241 provides M1 and M2 mode control signals according to the position of switch 94. These control signals are applied to the various circuits of the monitor and control unit to control and condition the circuits in accordance with the selected mode. When a reinfusion ratio is selected by switch 94, the M1 and M2 mode control signals are logic low to condition the circuits to the exchange mode. When the switch is positioned to the AUTOLOGOUS position both signals are logic high to condition the autologous mode. An additional SCALE switch position, which allows weight-indicative transducer circuit pulses to be applied to rate readout 93, is provided by M1 being logic low and M2 being logic high.

Figure 15:
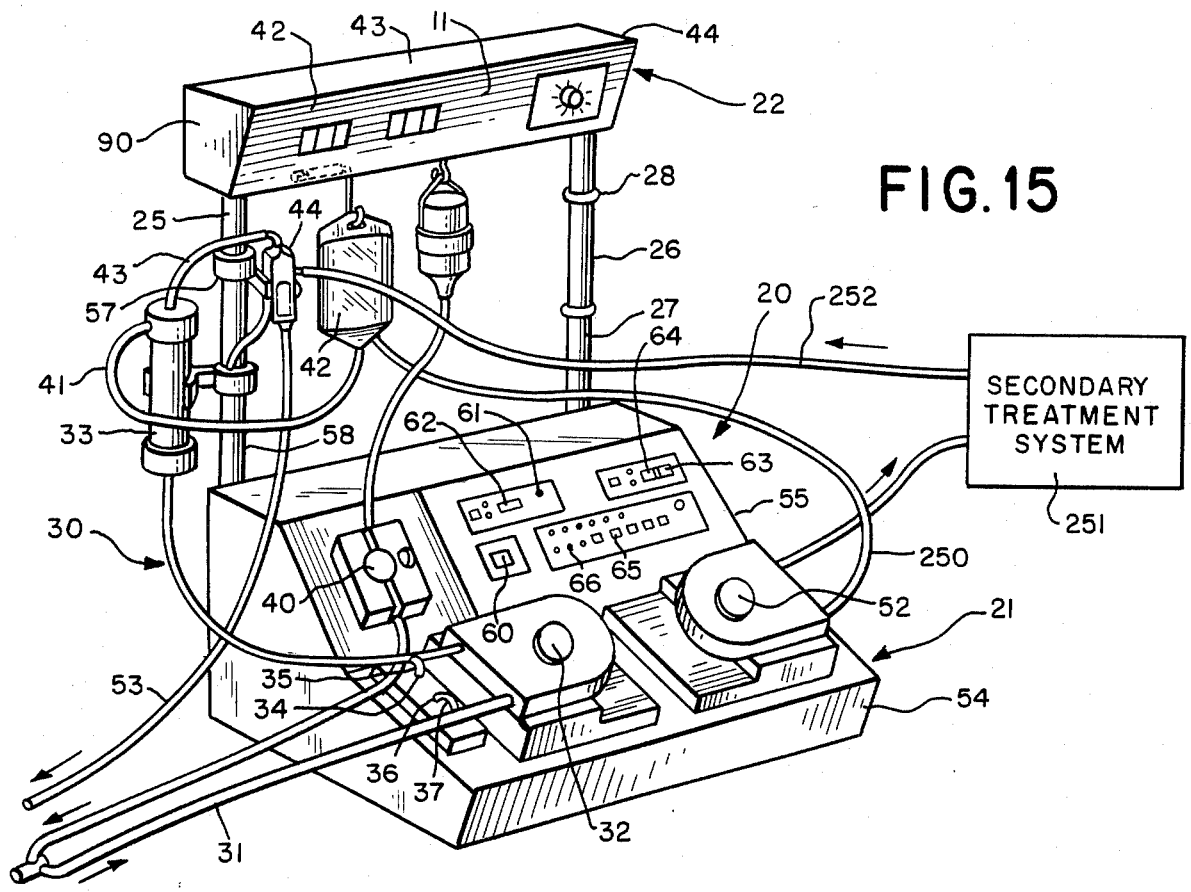
FIG. 15 is a perspective view of the plasmapheresis apparatus of FIG. 1 in conjunction with a fluid flow system for autologous mode operation.

In the autologous mode of plasmapheresis apparatus 20 an alternative flow system is provided wherein collected plasma is pumped from collection container 42 to a secondary processing system for treatment, and then returned to the chamber of bubble detector 44 for recombination with the processed blood and return to the donor. Referring to FIG. 15, the autologous mode flow system includes a tubing segment 250 which extends from an outlet port of collection container 42 through replacement 52 to a secondary plasma treatment system, and a tubing segment 252 which extends from the treatment system to the chamber of bubble detector 44. These tubing segments replace tubing segment 50 and replacement fluid container 51 in the exchange mode system shown in FIGS. 1 and 2.

Upon operation of pump 52 plasma is pumped from the collection container through treatment system 251, and back into the donor through bubble detector chamber 44. Various types of plasma treatment may be accomplished in the treatment system, including the removal of excess quantities of certain antigens. A constant quantity of plasma is automatically maintained in collection container 42 during autologous mode operation by varying the speed of the replacement pump so as to match its pumping rate to the rate of plasma collection in container 42.

Figure 16:
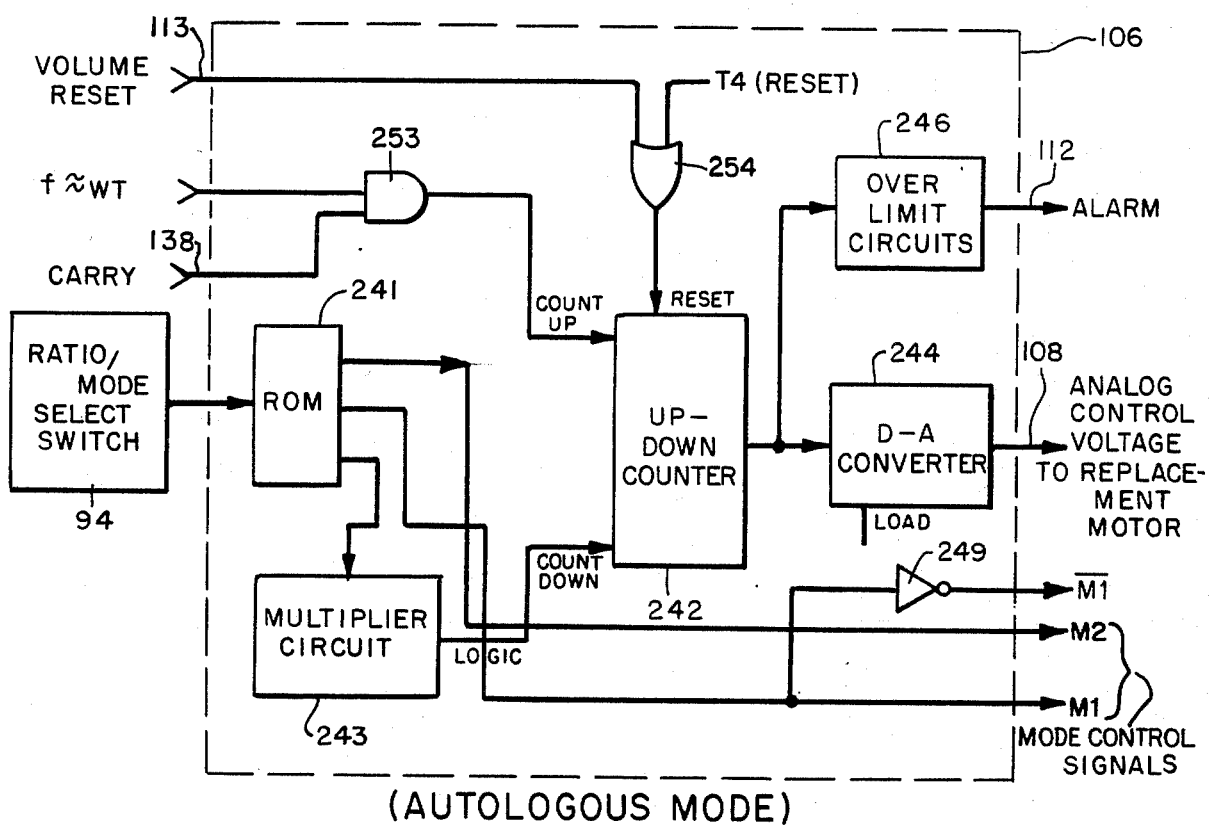
FIG. 16 is a simplified functional block diagram of the fluid replacement ratio control system of FIG. 13 configured in an autologous mode.

Referring to FIG. 16, when replacement ratio control circuits 106 are configured for autologous operation the variable frequency pulses developed by conversion circuit 101 are applied to the up-count input of up-down counter 242 through an AND gate 253. The remaining input of AND gate 253 is connected to carry line 138, so that when the carry line is positive, indicating a positive difference between present and stored collected plasma volume, the AND gate is enabled and counter 242 is caused to count up in response to the pulses. Rate multiplier circuit 243 is at this time conditioned by ROM 241 to a zero counting state; so that a continuous logic high output is applied by the multiplier circuit to the down count input of counter 242. This enables the counter to respond to the pulses applied to its up count input. No reinfusion pulses from volume derivation circuit 103 or tachometer pulses from replacement motor tachometer 77 are utilized in this operating mode.

An OR gate 254 allows the up-down counter 242 to be reset by either 1 hertz clock pulses or by a reset signal on the volume reset line 113. As in the ratio mode, over limit circuits 246 provide an alarm output in the event that the count in up-down counter 242 exceeds a predetermined limit, indicating that the balance in the plasma collection container 42 is not being maintained within limits.

Within volume derivation circuits 103 the M1 control signal developed by ROM 241 inhibits AND gates 136 and 139 (FIG. 6). This prevents the application of the $T_3$ (transfer) clock pulses otherwise applied to register 132 during each compute period. As a result, the register assumes and maintains the count of counter 130 at the time the apparatus is conditioned to the autologous mode. Counter 130 continues to receive and count pulses developed by transducer conversion circuits 102 during each measurement interval, and binary adder 131 develops the difference between each successive count of counter 130 and the stored count of register 132. However, the collection pulses developed by parallel-to-serial converter 134 are not applied to display counter 135 by reason of AND gate 136 being inhibited by the M1 mode control signal. Similarly, rate indicative pulses from shift register 200 are not applied to display counter 202 by reason of AND gate 201 being inhibited by the M1 mode control signal. Thus, in the autologous mode, readouts 62 and 64 are both rendered inoperative.

The application of transducer output 138 pulses to the up-down counter is initiated upon the carry output of binary adder 131 becoming positive. This occurs when the count reached by input counter 130 exceeds the count stored by register 132. Upon the carry output becoming positive, AND gate 247 is enabled and all subsequent transducer pulses developed by frequency divider 126 are applied to up-down counter 242. This causes counter 242 to count up, resulting in the development of an analog control voltage by converter 244 upon occurence of the next occurring $T_3$ (latch) clock signal. The analog control voltage causes replacement motor 76 to operate to withdraw fluid from collection container 42. When sufficient fluid has been withdrawn from the collection container such that the count reached by counter 130 does not exceed the count stored in register 132, the carry output of binary adder 131 no longer becomes positive for any portion of the measurement interval and no transducer circuit output pulses are applied to up-down counter 242. Consequently, no analog control voltage is produced by converter 244 and the replacement motor 76 does not operate.

Figure 17:
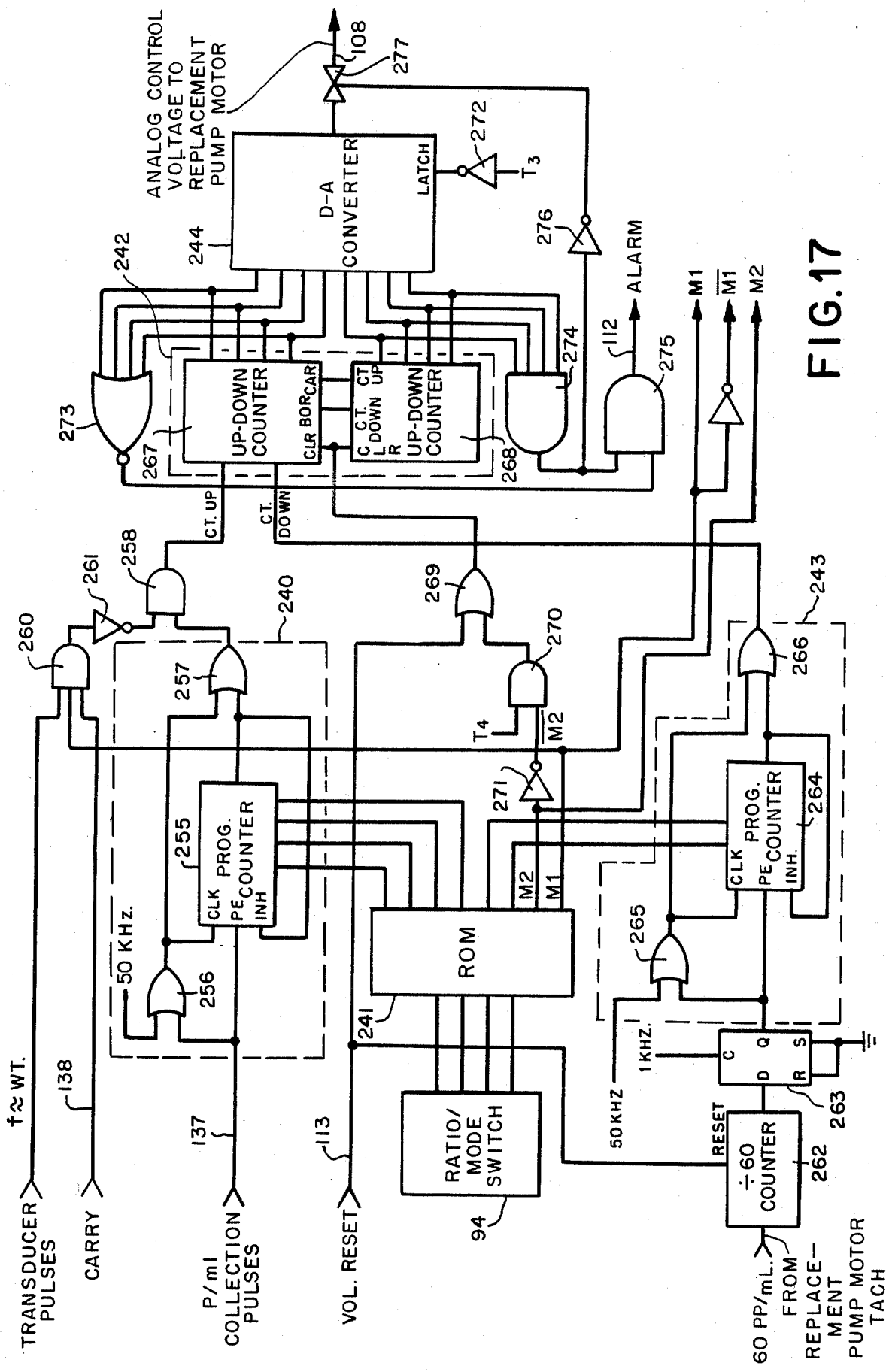
FIG. 17 is a simplified schematic diagram of the fluid replacement rate control system of FIGS. 13 and 16.

Referring to FIG. 17, multiplier circuit 240 may comprise a programmable counter 255 having a parallel-enable (PE) input to which collection pulses developed by volume derivation circuits 103 on line 137 are applied. This counter is programmed to provide a predetermined multiplication factor by means of a binary, signal developed by ROM 241. To enable the programmable counter to provide rate multiplication of the collection pulses clocked at 1 kHZ, the counter is clocked at 50 kHz by clock signals supplied to its clock input through an OR gate 256. Upon the occurrence of a collection pulse the programmable counter is enabled in its parallel mode, causing the binary count applied by ROM 241 to be parallel-loaded. At the same time OR gate 256 is enabled to allow the 50 kHz clock pulses to clock programmable counter 260 from the parallel-loaded count to zero. While the counter is counting, the output of the counter allows 50 kHZ clock pulses to be applied through OR gates 257 and 258 to the count up input of up-down counter 242. Upon reaching zero, counter 255 provides an output which is applied to the inhibit input of the counter to inhibit further counting activity, and to one input of an OR gate 257 to inhibit the application of 50 kHz clock pulses to counter 242.

In the autologous mode the remaining input of AND gate 258 is alternatively supplied with $f \approx$ wt. transducer output pulses representing increments of weight on the transducer through an AND gate 260 and an inverter 261. The transducer pulses are applied to one input of the AND gate, and the other input of the AND gate is connected to the carry line 138 associated with binary adder 131 (FIG. 6). The remaining input of AND gate 260 is connected to the M1 control line output of ROM 241. As a result, AND gate 260 is inhibited except when selector switch 94 is set to operate in an autologous mode. In this mode the M1 control line assumes a logic high and AND gate 260 is enabled by carry line 138 when the count of transducer pulses by counter 130 in any measurement interval exceeds the reference count stored in register 132 at the beginning of the autologous procedure. When AND gate 260 is enabled transducer output pulses are applied through AND gate 260, inverter 261 and AND gate 258 to counter 242. In this mode a binary zero is applied to programmable counter 255 by ROM 241 to force a logic high at the other input of AND gate 258.

Pulses from the replacement motor tach are applied to a divide-by-sixty counter 262 which provides one infusion pulse for each sixty tach pulses. In the illustrated plasmapheresis apparatus this corresponds to one pulse per milliliter of fluid pumped by the replacement pump. The output from counter 262 is applied to a D-type flip-flop 263 which functions in a conventional manner in response to a 1 kHz clock pulse applied to its clock input to provide the synchronous pulse for each output of counter 262. The synchronized pulse is applied to the second rate multiplier circuit 243, which takes the form of a programmable counter 264.

This counter is conditioned to either a zero, four or ten counting state by ROM 241 upon the application of each replacement pulse. OR gate 265 prevents 50 kHz clock pulses from being applied to counter 264 during the infusion pulse. Upon completion of the pulse counter 264 is counted down to zero by 50 kHz pulses applied to its clock input until a zero count is reached, at which time the output assumes a logic zero which inhibits further activity by the counter. While counter 264 is counting the 50 kHz clock pulses are applied through an OR gate 266 to the down count input of up-down counter 242. Upon counter 243 reaching zero OR gate 261 is inhibited to prevent the further application of pulses to counter 242.

The up-down counter 242 may comprise two separate up-down ounters 267 and 268 connected together in a conventional manner to operate as the single counter of FIGS. 13 and 16. Specifically, the carry output of up-down counter 267 is connected to the count up input of counter 268, the borrow output of counter 267 is connected to the count down input of counter 268, and the clear inputs of the counters are connected together. Total volume reset control signals on reset line 113 are applied to the clear inputs of counters 267 and 268 through an OR gate 269. During each operation in the prime mode, $T_4$ (reset) clock pulses are also applied to the clear inputs of the counters through an AND gate 270 and the remaining input of OR gate 269. AND gate 270 is enabled by ROM 241 when switch 94 is positioned in either the AUTOLOGOUS mode or in the SCALE mode. This is accomplished by applying the M2 control signal developed by ROM 241 through an inverter 271 to the remaining input of AND gate 270.

The outputs of up-down counters 267 and 268 are applied to digital-to-analog converter 244. This converter is of the latch type, and is latched during each compute interval by a $T_3$ (load) clock pulse applied through an inverter 272 to the latch input of the converter. Consequently, in operation counters 242 reach their final count by reason of the sequence commanded by clock pulses $T_1$-$T_2$, but the analog output of converter 244 does not change until a $T_3$ clock pulse commands a latch operation.

The binary outputs of counters 267 and 268 are monitored for an overlimit condition by NOR gate 273 and AND gate 274, which together comprise the previously identified overlimit circuits 246 (FIGS. 13 and 14). The output of NOR gate 273, which has as its inputs the four least significant digits of the counter output signal, is applied through an AND gate 275 to the alarm circuits of the apparatus through line 112. The output of AND gate 274, which has as its inputs the four most significant digits of the counter output signal, is applied to the remaining input of AND gate 275 to signal an alarm condition. In addition, the output of AND gate 274 is applied through an inverter 276 to an analog switch device 277, which interrupts application of the analog control voltage developed by digital-to-analog converter 244 to the processor along control line 108.

In operation, during the exchange mode, collection pulses are rate-multiplied by programmable counter 240 according to a factor set by ROM 241 and applied through OR gate 257 and AND gate 258 to the count up input of up-down counters 267 and 268. At the same time, replacement motor tach output pulses from the processor are applied through counter 262 and flip-flop 263 to programmable counter 264. This counter applies a rate multiplication according to a factor set by ROM 241 to develop pulses for application to the count down input of counters 267 and 268 through OR gate 266. The ratio between counters 255 and 264 is set by ROM 241 in accordance with the setting of ratio/mode switch 94. Counters 267 and 268 provide an output signal dependent on the cumulative difference between the rationalized collection pulses and rationalized tach pulses. This binary signal is periodically recognized by digital-to-analog converter 244 upon occurrence of a $T_3$ (latch) clock pulse to produce an analog control voltage which is applied to the replacement motor through control line 108.

In the event of an initial over limit alarm condition, indicated by the presence of an all logic low signals at the four least significant digits monitored by OR gate 273, OR gate 273 sounds an alarm in the processor through AND gate 275 and line 112. In the event a further limit is exceeded, accompanied by the four most significant digits becoming logic high, then AND gate 274 functions to interrupt the analog control signal by opening analog switch 277.

Counters 267 and 268 are reset only upon initial power-up, or during operation in the prime mode, or by $T_4$ pulses through AND gate 270 and OR gate 269 when operating in the autologous mode. The M2 control signal of ROM 271 inhibits AND gate 270 to prevent $T_4$ (reset) clock pulses from effecting a reset during the exchange mode.

In the autologous mode ROM 241 programs a binary zero into programmable counters 255 and 264. This results in these counters applying a logic high output to OR gates 257 and 266. The M1 control line output of ROM 241 enables AND gate 260 so that in the presence of a logic high on carry line 138 AND gate 260 allows frequency-variable weight-dependent transducer pulses to be applied to the countup input of counters 267 and 268 through AND gate 260, inverter 261 and AND gate 258. Counters 267 and 268 are now periodically reset by $T_4$ (reset) clock pulses during each compute interval by reason of AND gate 270 being enabled by the M2 output of ROM 241 through inverter 271. The $T_4$ (reset) clock pulses are applied through OR gate 269 to the counters.

When switch 94 is set to the SCALE position, a logic low is developed on control line M1 and a logic high is developed on control line M2. This causes AND gate 205 (FIG. 11) to be enabled, allowing the $f \approx$ wt. signals developed at the output of counter 102 to be applied through OR gate 204 to the display counter 202 of rate derivation circuit 104. Since this counter continues to be latched and reset by $T_2$ and $T_4$ clock signals at one second intervals, counter 202 assumes a count proportional to the total weight of the collection container and the collected plasma. This count is displayed by rate display 93.

The SCALE position of switch 94 allows the operator to verify proper operation of the transducer circuits. Prior to performing a plasmapheresis procedure, the operator suspends a known weight from the transducer and compares the resulting reading on readout 93 with a reading known to be correct. If the two readings agree, the transducer is operating properly.

Figure 18:
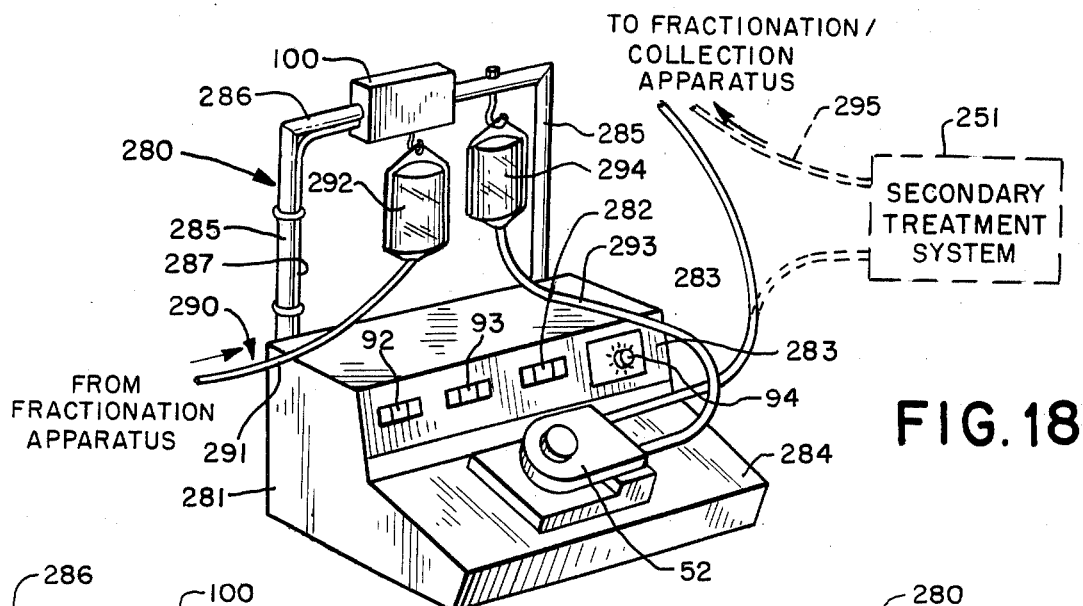
FIG. 18 is a perspective view of a collection monitor and replacement fluid pump apparatus constructed in accordance with the invention, for use in conjunction with continuous-flow blood fractionation apparatus.

Referring to FIG. 18, the volume derivation, rate derivation and replacement ratio control circuits of collection monitor and replacement ratio control unit 22 may be incorporated with the replacement fluid pump 52 in a separate standalone collection monitor and replacement control apparatus 280 for use with existing blood fractionation filter and centrifugal-type systems (not shown). The apparatus may be housed in a housing 281 having a sloping top panel 283 on which the volume collected display 92, collection rate display 93, and ratio/mode select switch 94 of the previously described plasmapheresis apparatus 20 are located. In addition, a replacement volume display 282 may be provided. The housing also includes a sloping bottom panel 284 on which the replacement pump 252 of the previously described apparatus is located.

A pair of vertical support poles 285 attached to the rear of the housing support a horizontal bar 286. The transducer circuit 100 is mounted on the horizontal bar to provide a signal having a voltage level proportional to weight on the transducer, as previously described. A cable 287 connects the transducer circuit to circuitry within housing 281.

The monitor and collection apparatus 281 may be utilized in either an exchange mode or in an autologous mode. In the exchange mode, a flow system 290 installed on the apparatus includes a tubing segment 291 which supplies plasma (or other blood fraction) separated in the associated fractionation apparatus to a collection container 292 suspend from the transducer. As the volume of fluid in container 292 increases, replacement fluid is automatically pumped by replacement fluid pump 52 from a replacement fluid container 294 through a tubing segment 293 to the fractionation apparatus for recombination with the plasma-deficient blood and subsequent return to the donor.

In the autologous mode flow system 290 is configured as shown by the broken lines in FIG. 18. Replacement fluid container 294 is not provided. Replacement fluid pump 52 pumps fluid from a second port on collection container 292 through tubing segment 293 to secondary treatment system 251, wherein the concentration of certain substances in the plasma may be altered by one or more processes. The processed plasma is returned to the fractionation apparatus by a tubing segment 295 for recombination and return to the donor.

Figure 19:
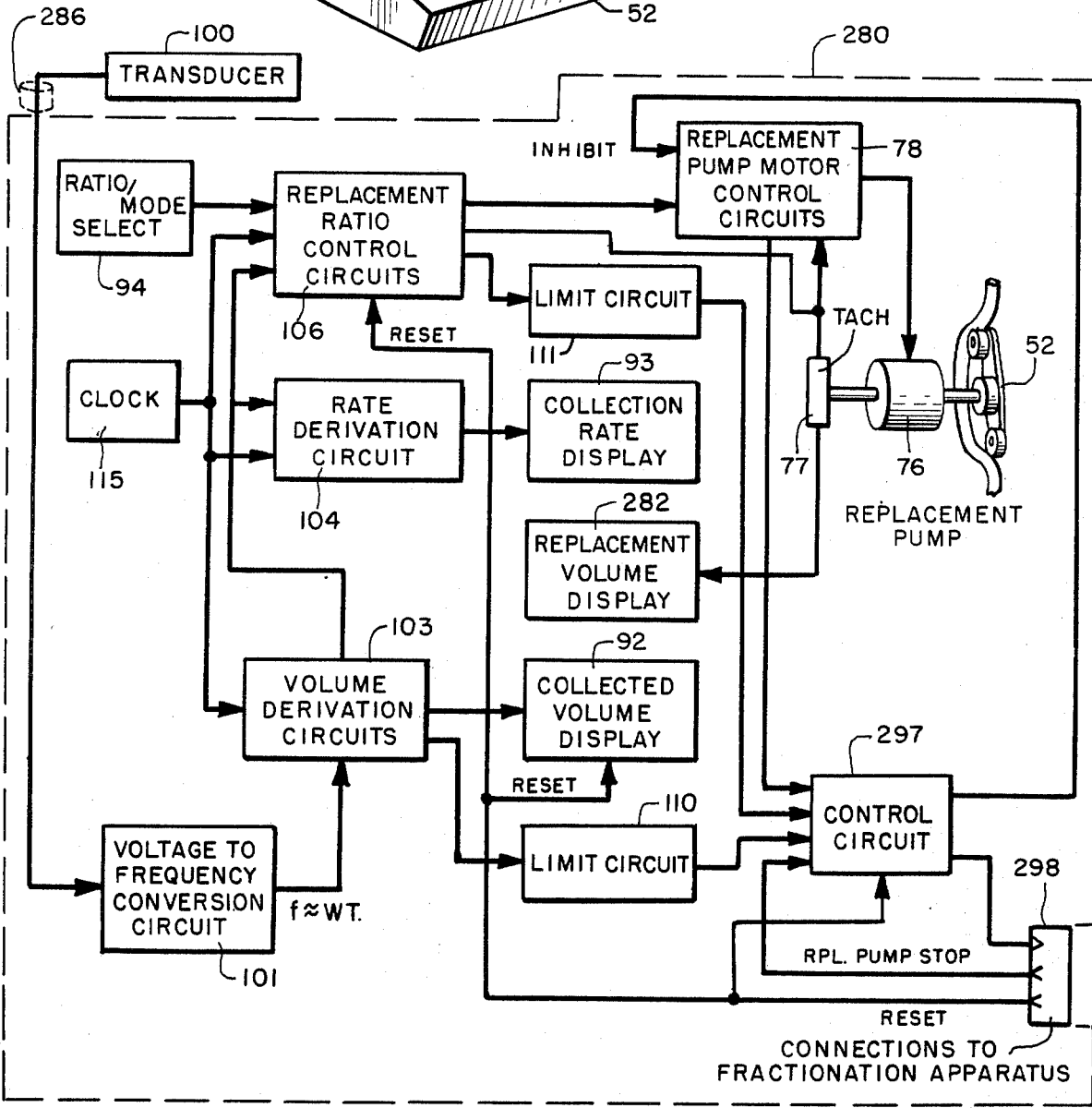
FIG. 19 is a functional block diagram showing the principal components of the collection monitor and replacement fluid pump apparatus of FIG. 18.

As shown in FIG. 19, the circuitry of apparatus 280 may be similar to that of the pertinent portions of the processor unit 21 and the monitor and control unit 22 of plasmapheresis apparatus 20. The voltage-variable signal from transducer circuit 100 is converted to a $f \approx$ wt. signal in conversion circuits 101 and applied to volume derivation circuit 103, wherein a volume collected output signal is developed for display 92, and collection pulses are developed for rate derivation circuit 104 and replacement control circuit 106. Rate derivation circuit 104 processes the collection pulses to provide a collection rate display 93. Replacement control circuits 106 compare the collection pulses with pulses from the tachometer 77 of replacement pump motor 76 and provide an analog output signal which controls the speed of motor 76 through motor control circuits 78 to maintain a ratio selected by switch 94. The output of tachometer 77 is also applied to replacement volume display 282 wherein a cumulative count is developed for display as total volume in milliliters of replacement fluid added. A clock 115 provides necessary timing pulses for the various circuits of the apparatus.

Operation of apparatus 280 is coordinated with the operating mode of the associated fractionation apparatus by a control circuit 297, which receives over-limit signals from limit circuits 110 and 111 and a stall signal from motor control circuit 78, and provides an inhibit output to the motor control circuit and mode control signals to the other circuits. Stop, start and reset connections between control circuit 297 and the associated apparatus are provided through a connector 298.

In operation, apparatus 280 may be placed in any convenient location for connection to the fractionation apparatus. After the tubing and electrical connections have been made, operation is completely automatic; a predetermined volume ratio being maintained in the exchange mode, and a predetermined collected volume being maintained in the collection container in the autologous mode.

Thus, the invention provides a system for controlling the flow of replacement fluid for the blood fraction removed, and for maintaining an operator-selected ratio between the volume of fraction collected and the volume of fluid replaced. The selected ratio is maintained notwithstanding variations in plasma collection rate or disturbances to the plasma collection container, thus avoiding the need for constant attention on the part of the operator and providing for more accurate control and monitoring of the fractionation process. Furthermore, the system includes internal safeguards and alarms which alert the operator to malfunctions, and a system by which the operation and control of the associated processor apparatus is integrated with that of the monitor and control device.

Additional features of the invention include the ability to operate in an autologous mode wherein a predetermined fluid level is maintained in the fraction collection container, and in a scale mode wherein the actual weight of the collection container and collected content may be readily determined. Furthermore, the invention may be provided in a stand-alone unit having a self-contained replacement fluid pump for use in conjunction with a blood fractionation apparatus for monitoring the collection of a blood fraction or for adding replacement fluid to processed blood at an automatically maintained rate.

While the invention has been shown in conjunction with blood fractionation apparatus, it will be appreciated that the invention may be used in other applications and procedures where a ratio between a collected fluid and a replacement fluid are to be automatically maintained, or where a collected fluid component is to be removed from a collection container for processing concurrently with its collection in the container.

While particular embodiments of the invention have been shown and described it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. A control system for a fluid flow system having a collection container for collecting a fluid component which has been separated from a whole fluid and a variable speed replacement fluid pump for adding a replacement fluid to the depleted whole fluid, said control system being operative for maintaining a desired ratio between the volume of fluid component collected in the collection container and the volume of replacement fluid added to the depleted whole fluid and comprising:

weight responsive means including an electrical transducer operatively associated with the collection container for providing at predetermined measurement intervals an output signal indicative of the volume of the fluid component in the collection container;

first comparison means for repetitively comparing successive output signals of said weight responsive means to develop difference signals indicative of incremental units of fluid volume added to the collection container during each of said measurement intervals, said first comparison means being also operative for comparing each of said difference signals to a predetermined range of signals indicative of collection rates obtainable by the flow system during normal operation;

means for converting only said difference signals which fall within said predetermined range into corresponding collection signals, whereby an aberrant difference signal developed as a result of a physical disturbance of the collection container and not as a result of normal operation of the flow system will not develop a corresponding aberrant collection signal;

first rate multiplier means responsive to each of said collection signals for providing a first comparison signal;

pump responsive to operation of the replacement fluid pump for providing output signals indicative of the volume of replacement fluid conveyed by the replacement fluid pump during each of said measurement intervals;

second rate multiplier means responsive to each of said output signals of said pump responsive means for providing a second comparison signal; and second comparison means for comparing at the end of each of said measurement intervals said associated first comparison signal with said associated second comparison signal to develop an output signal for varying the speed of the replacement fluid pump in proportion to the difference between said first and second comparison signals to maintain the desired volume ratio.

2. A control system as defined in claim 1
   wherein said output signal of said weight responsive means comprises output pulses proportional in number to the volume of the fluid component in the collection container at the end of each of said measurement intervals;

wherein said first comparison means is operative for comparing said successive output pulses to develop said difference signal which comprise difference pulses proportional in number to the incremental change in fluid volume during each of said measurement intervals and for comparing each of said difference pulses to said predetermined range which comprises a predetermined range of pulses indicative of collection rates normally obtainable by the flow system; and wherein said conversion means is responsive only to said difference pulses which fall within said predetermined range for producing said corresponding collection signals in the form of collection pulses.

3. A control system as defined in claim 2 wherein said pump responsive means includes a tachometer for producing said output signal which comprises output pulses proportional in number to the volume of replacement fluid conveyed by the replacement fluid pump during each of said measurement intervals.

4. A control system as defined in claim 1 wherein said first and second rate multiplier means include programmable counters.

5. A control system as defined in claim 4 and further including a user-operated ratio selection switch, and a read only memory responsive to the setting of said selector switch for providing ratio-determining control signals to said programmable counters.

6. A control system as defined in claim 1 wherein said second comparison means includes an up-down counter and a binary-to-analog converter, and wherein said up-down counter provides an output signal proportional to the difference between said first and second comparison signals for application to said converter and said converter provides an analog control voltage proportional to said counter output signal for varying the speed of the replacement fluid pump.

7. A control system as defined in claim 6 and further including limit means providing an alarm output upon said up-down counter exceeding a predetermined maximum count.

* * * * *

UNITED STATES PATENT AND TRADEMARK OFFICE
CERTIFICATE OF CORRECTION

PATENT NO. : 4,582,598
DATED : April 15, 1986
INVENTOR(S) : Arnold C. Bilstad and John T. Foley It is certified that error appears in the above-identified patent and that said Letters Patent are hereby corrected as shown below:

In claim 1, at column 22, line 33 should read --pump responsive means responsive to operation of the replacement--.

In claim 2, at column 22, line 57, "signal" should read --signals--.

Signed and Sealed this

Fifteenth Day of July 1986

[SEAL]

Attest:

DONALD J. QUIGG

Attesting Officer

Commissioner of Patents and Trademarks